United States Patent [19]

Schaap

[11] Patent Number: 4,857,652
[45] Date of Patent: Aug. 15, 1989

[54] CHEMILUMINESCENT 1,2-DIOXETANE COMPOUNDS

[75] Inventor: Arthur P. Schaap, Detroit, Mich.

[73] Assignee: Board of Governors of Wayne State University, Detroit, Mich.

[21] Appl. No.: 235,199

[22] Filed: Aug. 23, 1988

Related U.S. Application Data

[62] Division of Ser. No. 887,139, Jul. 17, 1986.

[51] Int. Cl.⁴ ............................................. C07D 321/00
[52] U.S. Cl. .................................. 549/510; 549/511; 549/414; 549/214; 549/332
[58] Field of Search ................ 549/214, 332, 510, 511

[56] References Cited

U.S. PATENT DOCUMENTS 3,720,622 3/1973 Bollyky .............................. 568/301
4,315,998 2/1982 Neckers et al. .................. 525/369.3

FOREIGN PATENT DOCUMENTS 1044639 12/1979 Canada .
2383404 10/1978 France .
57-042686 3/1982 Japan .

OTHER PUBLICATIONS

F. McCapra, Chem. Commin., 155, (1968).
Shimomura, O., et al., Photochem. Photobiol., 30, 89, (1979).
Kopecky et al., Can. J. Chem., 47, 709, (1969).
Bartlett, et al., J. Amer. Chem. Soc., 92, 3223, (1970).
Mazur et al., J. Amer. Chem. Soc., 92, 3225, (1970).
Schaap, et al., J. Amer. Chem. Soc., 99, 1270, (1977).
Zaklika et al., J. Amer. Chem. Soc., 100, 318, (1978) & 100, 4916, (1978).
Zaklika et al., Photochem. Photobiol., 30, 35, (1979).
Schaap et al., Organic Photochemical Synthesis, II, 49, (1976).
Schaap et al., J. Amer. Soc., 101, 4016, (1979), & 97, 3741, (1975).
Wieringa et al., Tetrahedron Lett., 169, (1972).
Turro et al., J. Amer. Chem. Soc., 97, 7110, (1975).
Adam et al., Z. Natuforsch., 39b, 679, (1984).
Wynberg et al., In Bioluminescence & Chemiluminescence, DeLuca and McElroy (Eds.), Academic Press, N.Y., p. 687, (1981).
McCapra et al., J. Chem. Soc., Chem. Commun., 944, (1977).
Adam, W., et al., Chem. Ber., 116, 839, (1983).
Geller, G. G., et al., Tetrahedron Lett., 673, (1983).
Schaap et al., Tetrahedron Lett., 2943, (1982).
Handley, R. S., et al., Tetrahedron Lett., 3183, (1985).
Schaap, et al., J. Amer. Chem. Soc., 104, 3504, (1982).
Corey et al., J. Amer. Chem. Soc., 94, 6190, (1972).
Kricka, L. J., Ligand–Binder Assays, Marcel Dekker, Inc., N.Y., pp. 170 & 199, (1985).
Sunthankar et al., J. Org. Chem., 16, 8, (1951).
Patolia & Trivedi, Indian J. Chem., 22B, 444, (1983).
Davies et al., J. Org. Chem., 23, 307, (1958).
Wilson, T., et al., J. Amer. Chem. Soc., 93, 4126, (1971).
McMurry, J. Am. Chem. Res., 16:405–411, (1983).
McMurry, J. E. and D. D. Miller, J. Am. Chem. Soc., 105:1660–1661, (1983).

Primary Examiner—Richard L. Raymond
Assistant Examiner—Ba Trinh
Attorney, Agent, or Firm—Ian C. McLeod

[57] ABSTRACT

Novel light producing 1,2-dioxetanes are described of the formula

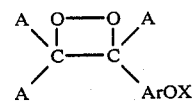

wherein ArOX is an aryl ring substituted with an X oxy group and A are passive organic groups which allow the 1,2-dioxetane to produce light when triggered by removing X. X is a chemically labile group which is removed by an activating agent. The 1,2-dioxetane compounds can be triggered to produce light at room temperatures.

14 Claims, 2 Drawing Sheets

CHEMILUMINESCENT 1,2-DIOXETANE COMPOUNDS

BACKGROUND OF THE INVENTION

(1) Statement of the Invention

This is a divisional of co-pending application Ser. No. 887,139 filed on July 17, 1986.

The present invention relates to chemiluminescent 1,2-dioxanetane compounds which can be triggered by an activating agent to generate light. In particular, the present invention relates to stable aryl group substituted 1,2-dioxetanes which contain an activatable oxide group (OX) which is ring substituted in the aryl group, wherein the stable 1,2-dioxetane forms an unstable 1,2-dioxetane compound by removal of X which decomposes to light and two carbonyl containing compounds

(2) Prior Art

1. Mechanisms of Luminescence. Exothermic chemical reactions release energy during the course of the reaction. In virtually all cases, this energy is in the form of vibrational excitation or heat. However, a few chemical processes generate light or chemiluminescence instead of heat. The mechanism for light production involves two steps: (1) thermal or catalyzed decomposition of a high energy material (generally a peroxide) yields one of the reaction products in a triplet or singlet electronic excited state and (2) emission of a photon (fluorescence or phosphorescence) from this excited species produces the light observed from the reaction.

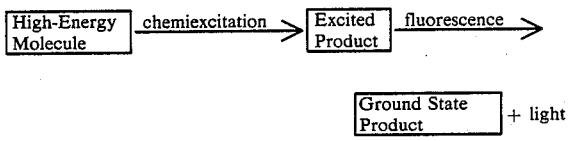

2. Dioxetane Intermediates in Bioluminescence. In 1968 McCapra proposed that 1,2-dioxetanes might be the key high-energy intermediates in various bioluminescent reactions including the firefly system. (F. McCapra. *Chem. Commun.*, 155 (1968)). Although this unstable dioxetane intermediate has not been isolated nor observed spectroscopically, unambiguous evidence for its intermediacy in this biochemical reaction has been provided by oxygen-18 labelling experiments (O. Shimomura and F. H. Johnson, *Photochem. Photobiol.*, 30, 89 (1979)).

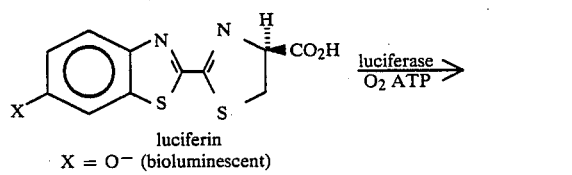

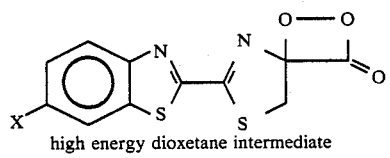

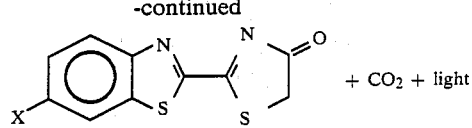

3. First Synthesis of Authentic 1,2-Dioxetanes. In 1969 Kopecky and Mumford reported the first synthesis of a dioxetane (3,3,4-trimethyl-1,2-dioxetane) by the base-catalyzed cyclization of a beta-bromohydroperoxide. (K. R. Kopecky and C. Mumford, *Can. J. Chem.*, 47, 709 (1969)). As predicted by McCapra, this dioxetane did, in fact, produce chemiluminescence upon heating to 50° C. with decomposition to acetone and acetaldehyde. However, this peroxide is relatively unstable and cannot be stored at room temperature (25° C.) without rapid decomposition. In addition, the chemiluminescence efficiency is very low (less than 0.1%). This inefficiency is due to two factors (1) the biradical nature of the mechanism for its decomposition and (2) the low quantum yield of fluorescence of the carbonyl cleavage products.

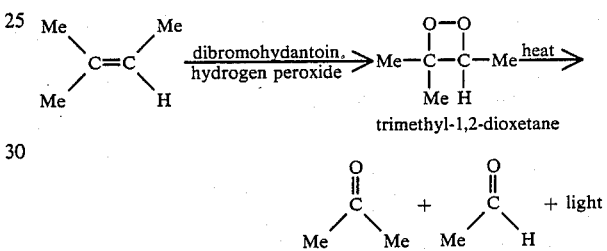

Bartlett and Schaap and Mazur and Foote independently developed an alternate and more convenient synthetic route to 1,2-dioxetanes. Photooxygenation of properly-substituted alkenes in the presence of molecular oxygen and a photosensitizing dye produces the dioxetanes in high yields. (P. D. Bartlett and A. P. Schaap, *J. Amer Chem. Soc.*, 92, 3223 (1970) and S. Mazur and C. S. Foote, *J. Amer. Chem. Soc.*, 92 3225 (1970)). The mechanism of this reaction involves the photochemical generation of a metastable species known as singlet oxygen which undergoes 2+2 cycloaddition with the alkene to give the dioxetane. Research has shown that a variety of dioxetanes can be prepared using this reaction (A. P. Schaap, P. A. Burns, and K. A. Zaklika, *J. Amer. Chem. Soc.*, 99, 1270 (1977); K. A. Zaklika, P. A. Burns, and A. P. Schaap, *J. Amer. Chem. Soc.*, 100, 318 (1978); K. A. Zaklika, A. L. Thayer, and A. P. Schaap, *J. Amer. Chem. Soc.*, 100, 4916 (1978); K. A. Zaklika, T. Kissel, A. L. Thayer, P. A. Burns, and A. P. Schaap, *Photochem Photobiol.*, 30, 35 (1979); and A. P. Schaap, A. L. Thayer, and K. Kees, *Organic Photochemical Synthesis*, II, 49 (1976)). During the course of this research, a polymer-bound sensitizer for

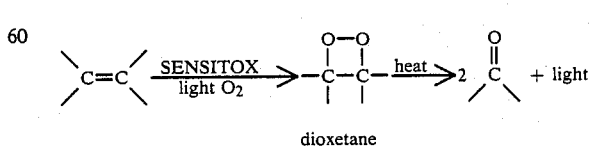

photooxygenations was developed (A. P. Schaap, A. L. Thayer, E. C. Blossey, and D. C. Neckers, *J. Amer. Chem. Soc.*, 97, 3741 (1975); and A. P. Schaap, A. L.

Thayer, K. A. Zaklika, and P. C. Valenti, *J. Amer. Chem. Soc.*, 101, 4016 (1979)). This new type of sensitizer has been patented and sold under the tradename SENSITOX TM (U.S. Pat. No. 4,315,998 (2/16/82); Canadian Patent No 1,044,639 (12/19/79)). Over fifty references have appeared in the literature reporting the use of this product 4. Preparation of Stable dioxetanes Derived from Sterically Hindered Alkenes. Wynberg discovered that photooxygenation of sterically hindered alkenes such as adamantylideneadamantane affords a very stable dioxetane (J. H. Wieringa, J. Strating, H. Wynberg, and W. Adam, *Tetrahedron Lett.*, 169 (1972)). A collaborative study by Turro and Schaap showed that this dioxetane exhibits an activation energy for decomposition of 37 kcal/mol and a half-life at room

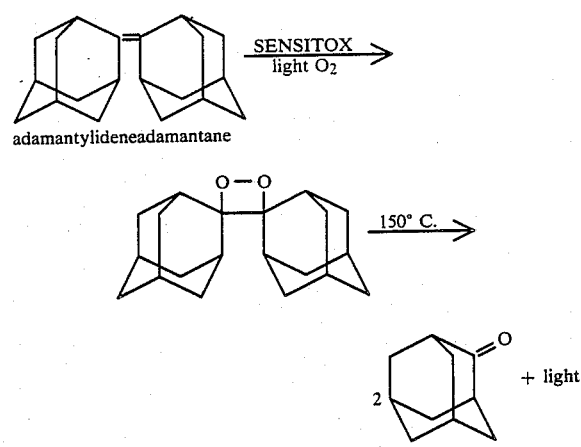

adamantylideneadamantane temperature (25° C.) of over 20 years (N. J. Turro, G. Schuster, H. C. Steinmetzer, G. R. Faler and A. P. Schaap, *J. Amer. Chem. Soc.*, 97, 7110 (1975)). In fact, this is the most stable dioxetane yet reported in the literature. Adam and Wynberg have recently suggested that functionalized adamantylideneadamantane 1,2-dioxetanes may be useful for biomedical applications (W. Adam, C. Babatsikos, and G. Cilento, *Z. Naturforsch.*, 39b, 679 (1984); H. Wynberg, E. W. Meijer, and J. C. Hummelen, *In Bioluminescence and Chemiluminescence*, M. A. DeLuca and W. D. McElroy (Eds ). Academic Press, New york, p. 687, 1981). However, use of this extraordinarily stable peroxide for chemiluminescent labels would require detection temperatures of 150° to 250° C. Clearly, these conditions are unsuitable for the evaluation of biological analytes in aqueous media. Further, the products (adamantanones) of these dioxetanes are only weakly fluorescent so that the chemiluminescent decomposition of these proposed immunoassay labels is very inefficient. McCapra, Adam, and Foote have shown that incorporation of a spirofused cyclic or polycyclic alkyl group with a dioxetane can help to stabilize dioxetanes that are relatively unstable in the absence of this sterically bulky group (F. McCapra, I. Beheshti, A. Burford, R. A. Hann, and K. A. Zaklika, *J. Chem. Soc., Chem. Commun.*, 944 (1977); W. Adam, L. A. A. Encarnacion, and K. Zinner, *Chem. Ber.*, 116, 839 (1983); and G. G. Geller, C. S. Foote, and D. B. Pechman, *Tetrahedron Lett.*, 673 (1983)).

5. Effects of Substituents on Dioxetane Chemiluminescence. The stability and the chemiluminescence efficiency of dioxetanes can be altered by the attachment of specific substituents to the peroxide ring (K. A. Zaklika, T. Kissel, A. L. Thayer, P. A. Burns, and A. P. Schaap, *Photochem. Photobiol.*, 30, 35 (1979); A. P. Schaap and S. Gagnon, *J. Amer. Chem. Soc.*, 104, 3504 (1982); A. P. Schaap, S. Gagnon, and K. A. Zaklika, *Tetrahedron Lett.*, 2943 (1982); and R. S. Handley, A. J. Stern, and A. P. Schaap, *Tetrahedron Lett.*, 3183 (1985)). The results with the bicyclic system shown below illustrate the profound effect of various functional groups on the properties of dioxetanes. The hydroxy-substituted dioxetane (X=OH) derived from the 2,3-diaryl-1,4-dioxene exhibits a half-life for decomposition at room temperature

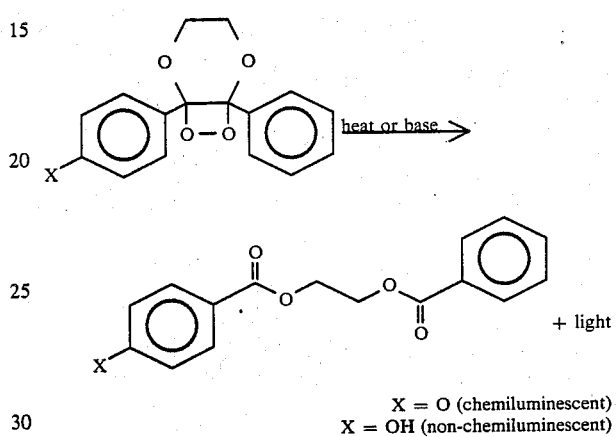

X = O⁻ (chemiluminescent)
X = OH (non-chemiluminescent)

(25° C.) of 57 hours and produces very low levels of luminescence upon heating at elevated temperatures. In contrast, however, reaction of this dioxetane with a base at −30/°C. affords a flash of blue light. Kinetic studies have shown that the deprotonated dioxetane (X=O−) decomposes $5.7 \times 10^6$ times faster than the protonated form (X=OH) at 25° C.

The differences in the properties of these two dioxetanes arise because of two competing mechanisms for decomposition (K. A. Zaklika, T. Kissel, A. L. Thayer, P. A. Burns, and A. P. Schaap, *Photochem. Photobiol.*, 30, 35 (1979); A. P. Schaap and S. Gagnon, *J. Amer. Chem. Soc.*, 104 3504 (1982); A. P. Schaap, S. Gagnon, and K. A. Zaklika, *Tetrahedron Lett.*, 2943 (1982); and R. S. Handley, A. J. Stern, and A. P. Schaap, *Tetrahedron Lett.*, 3183 (1985). Stable dioxetanes cleave by a process that requires approximately 25 kcal for homolysis of the O-O bond and formation of a biradical. An alternative mechanism for decomposition is available to dioxetanes bearing substituents such as O− with low oxidation potentials. The cleavage is initiated by intramolecular electron transfer from the substituent to the antibonding orbital of the peroxide bond. In contrast to the biradical mechanism, the electron-transfer process generates chemiluminescence with high efficiency.

Literature Examples Related to Triggering of dioxetanes (a) Base Triggering of Dioxetanes. The only example in the literature is described above (A. P. Schaap and S. Gagnon, *J. Amer. Chem. Soc.*, 104, 3504 (1982). The hydroxy-substituted dioxetane shown above is too unstable to be of use in any application. It has a half-life at 25° C. of only 57 hours. Neither the dioxetane nor the precursor alkene would survive the conditions necessary to prepare derivatives.

(b) Fluoride Triggering of dioxetanes. No examples appear in the literature with dioxetanes. Fluoride is used synthetically to desilylate alcohol derivatives. (E. J. Corey and A. Venkateswarlu, *J. Amer. Chem. Soc.*, 94, 6190 (1972).

(c) Enzymatic Triggering of Dioxetanes. No examples appear in the literature with dioxetanes. Enzymes have been used in Colorimetric Immunoassays and Fluorometric Immunoassays to remove phosphate, beta-D-galactoside, and other groups with resulting color development or formation of fluorescent materials (L. J. Kricka, In *Ligand-Binder Assays*, Marcel Dekker, Inc., New York, p. 170 (1985). There are numerous examples of chemiluminescence immunoassays (L. J. Kricka, *In Ligand-Binder Assays*, Marcel Dekker, Inc., New York, p. 199 (1985)) but no cases with a stable dioxetane that is triggered.

(d) Japanese Patent Application 57042686 filed Mar. 10, 1982 and French Patent No. 2,383,404 describe various unrelated dioxetanes. U.S. Pat. No. 3,720,622 describes unrelated light producing compounds.

OBJECTS

It is therefore an object of the present invention to provide novel stable 1,2-dioxetanes which can be decomposed with an activating agent to form light and two carbonyl compounds. Further it is an object of the present invention to provide 1,2-dioxetanes which are stable at room temperatures over an extended period of time. Further still it is an object of the present invention to provide 1,2-dioxetanes which are activatable by chemical and by biochemical means. Further still it is an object of the present invention to provide a method for the use of the stable 1,2-dioxetanes to generate light. These and other objects will become increasingly apparent by reference to the following description and the drawings.

In the Drawings

Figure 1:
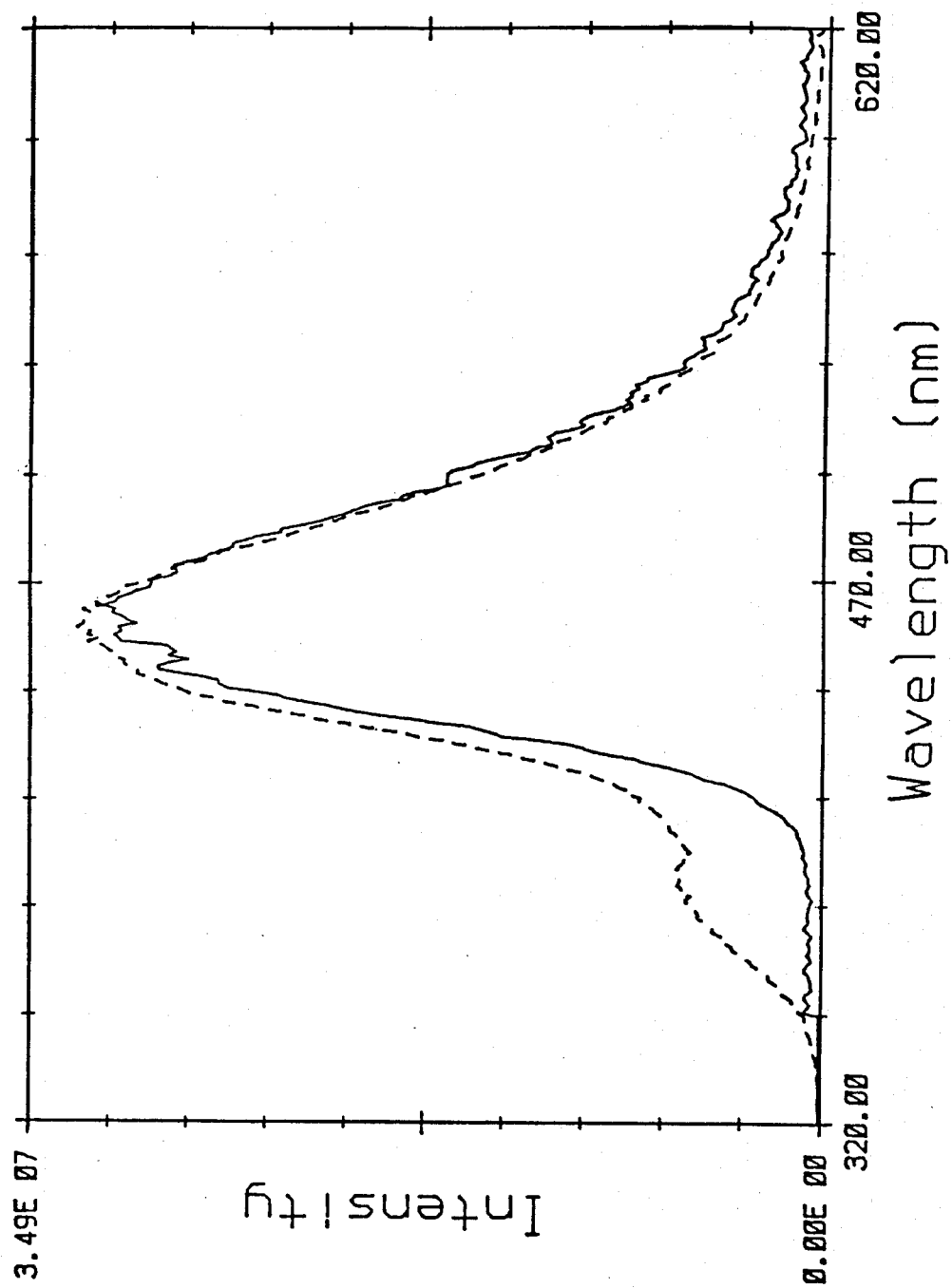
FIG. 1 is a graph showing light intensity as a function of wavelength for compound 2c described hereinafter and one of its carbonyl containing compound decomposition products, where the activating agent is a fluoride.

The present invention relates to a stable 1,2-dioxetane compound of the formula

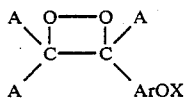

wherein ArOX an aryl group having an aryl ring substituted with an X-oxy group which forms an unstable oxide intermediate 1,2-dioxetane compound when triggered to remove X by an activating agent so that the unstable 1,2dioxetane compound decomposes to form light and two carbonyl containing compounds of the formula

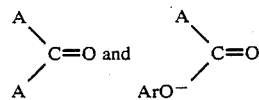

wherein X is a chemically labile group which is removed by the activating agent to form the unstable oxide intermediate 1,2-dioxetane and wherein A are passive organic groups which allow the light to be produced In particular the present invention relates to a stable 1,2-dioxetane compound of the formula

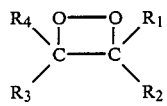

wherein $R_1$ and $R_2$ together and $R_3$ and $R_4$ together can be joined as spirofused alkylene and aryl rings, wherein at least one of $R_1$ and $R_2$ or $R_3$ and $R_4$ is an aryl group, having an aryl ring substituted with an X oxy- group which forms an unstable oxide intermediate 1,2 dioxetane compound when triggered to remove X by an activating agent selected from acids, bases, salts, enzymes, inorganic and organic catalysts and electron donors so that the unstable 1,2-dioxetane compound decomposes to form light and two carbonyl containing compounds of the formula:

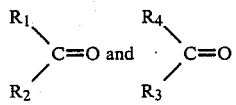

wherein those of $R_1$, $R_2$, $R_3$ or $R_4$ which are unsubstituted by an X-oxy group are carbon containing organic groups which provide stability for the stable 1,2-dioxetane compound and wherein X is a chemically labile group which is removed by the activating agent to form the unstable oxide intermediate Further the present invention relates to a stable dioxetane compound of the formula:

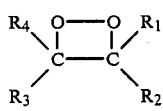

wherein $R_1$ is selected from alkyl, alkoxy, aryloxy, dialkyl or aryl amino, trialkyl or aryl silyloxy and aryl groups including spirofused aryl groups with $R_2$, wherein $R_2$ is an aryl group which can include $R_1$ and is substituted with an X-oxy group which forms an unstable oxide intermediate 1,2-dioxetane compound when activated by an activating agent to remove X selected from acids, bases, salts, enzymes, inorganic and organic catalysts and electron donors so that the unstable 1,2-dioxetane compound decomposes to form light and two carbonyl containing compounds of the formula:

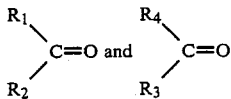

wherein X is a chemically labile group which is removed by the activating agent to form the unstable oxide intermediate and wherein R₃ and R₄ are selected from aryl and alkyl groups which can be joined together as spirofused polycyclic alkyl and polycyclic aryl groups.

Specifically the present invention relates to a a stable 1,2-dioxetane compound of the formula:

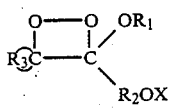 (I)

wherein $R_1$ is selected from lower alkyl containing 1 to 8 carbon atoms, $R_2$ is selected from aryl, biaryl and fused ring polycyclic aryl groups which can be substituted or unsubstituted, and $R_3C-$ is selected from polycyclic alkyl groups containing 6 to 30 carbon atoms, wherein OX is an oxy group substituted on an aryl ring which forms an unstable oxide intermediate 1,2-dioxetane compound when triggered to remove X by an activating agent selected from acid, base, salt, enzyme, inorganic and organic catalysts and electron donor sources and X is a chemically labile group which is removed by the activating agent to form the unstable oxide intermediate and wherein (I) decomposes in the presence of an activating agent to produce light and carbonyl containing compounds of the formula

 (II)

and

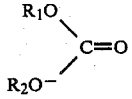 (III)

Finally the present invention relates to a stable 1,2-dioxetane compound of the formula:

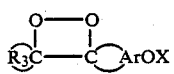 (II)

wherein ArOX is a spirofused aryl group containing a ring substituted X-oxy group, wherein OX forms an unstable oxide intermediate 1,2-dioxetane compound when triggered by an activating agent to remove X selected from acids, bases, salts, enzymes, inorganic and organic catalysts and electron donors, wherein X is a chemically labile group which is removed by the activating agent to form the unstable oxide intermediate 1,2-dioxetane so that the unstable 1,2-dioxetane compound decomposes to form light and two carbonyl containing derivatives of the formula

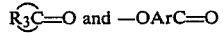

and wherein $R_3C-$ is selected from polycyclic alkyl groups containing 6 to 30 carbon atoms. In this structure R₁ and R₂ are joined together.

When R₁ is not combined with R₂ the group is preferably alkyl, alkoxy, dialkyl or arylamino trialkyl or aryl silyloxy. The alkyl groups preferably contain 1 to 8 carbon atoms. R₁ can also be cyclic aliphatic or aryl groups, including fused ring aryl compounds, containing 6 to 14 carbon atoms. When R₁ is combined with R₂ they provide an aryl group containing 6 to 30 carbon atoms R₂ is an aryl group substituted with an X oxy (OX) group The aryl containing group can be phenyl, biphenyl, fused phenyl and other aryl groups and can contain between 6 and 30 carbon atoms and can include other substituents. X is any labile group which is removed by an activating agent. The OX group can be for instance selected from hydroxyl, alkyl or aryl carboxyl ester, inorganic oxy acid salt, particularly a phosphate or sulfate, alkyl or aryl silyloxy and oxygen pyranoside groups.

R₃ and R₄ can be the same as R₁. In the following Examples, R₃ and R₄ are combined together to form a polycyclic alkylene group, particularly for ease of synthesis and comparison; however any organic group can be used. Preferably the polycyclic alkylene group contains 6 to 30 carbon atoms.

The stable 1,2-dioxetane compounds have relatively long ½ lives at room temperatures (20°-35° C.) even though they can be triggered by the activating agent. All of the prior art compounds are either unstable at room temperatures or require temperatures of 50° C. or above in order to be thermally decomposed which is impractical for most applications.

The activating agent may be chemical or enzymatic. In some cases (F⁻) 1 equivalent is required and in others (enzymatic) only a very small amount is used The agents are described in any standard chemical treatise on the subject and include acids, bases, salts, enzymes and other inorganic, organic catalysts. The agent used will depend upon the conditions under which the stable 1,2-dioxetane is to be activated and how labile the X group is on a particular 1,2-dioxetane. Electron donors can be used to remove X which can include reducing agents as well as electrical sources of electrons.

The 1,2-dioxetane decomposes to form carbonyl containing compounds and light. An unstable 1,2-dioxetane intermediate is formed of the formula:

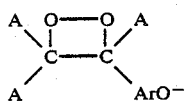

In general an —ArOX substituted 1,2-dioxetanes are formed by addition of oxygen to the appropriate alkene These alkenes are synthesized through an alkyl or aryl silyloxyaryl ring substituted intermediate. Thus the appropriate ketones of the formula:

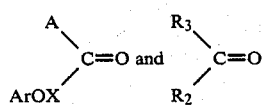

are reacted in the presence of lithium aluminum hydride or other metal hydride in a polar organic solvent, particularly tetrahydrofuran, with a transition metal halide salt, particularly titanium chloride, and a tertiary amine base. The reaction is generally conducted in refluxing tetrahydrofuran and usually goes to completion in about 4 to 24 hours.

1,2-Dioxetane Compounds Synthesized

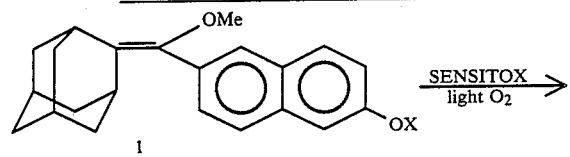

1

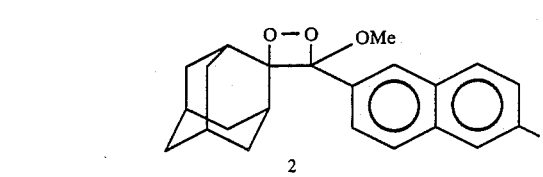

2

(a) OX is replaced by H
(b) X = H
(c) X = Si(t-Bu)Me$_2$
(d) X = Si(t-Bu)Ph$_2$
(e) X = COMe

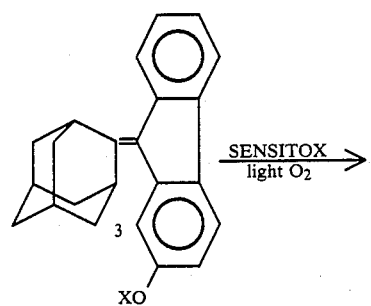

3

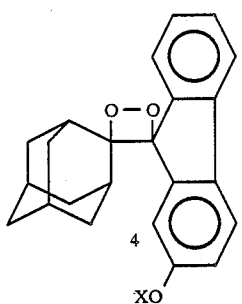

4

(a) X = H
(b) X = Si(t-Bu)Me$_2$

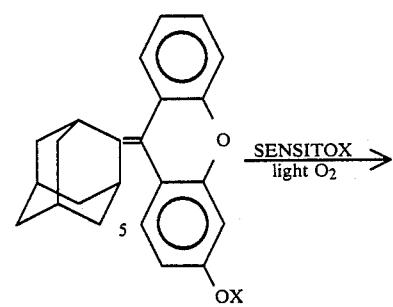

5

-continued
1,2-Dioxetane Compounds Synthesized

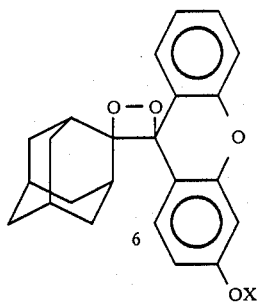

6

(a) X = H
(b) X = Si(t-Bu)Me$_2$
(c) X = COMe
(d) X = PO$_3$(Et$_4$N)$_2$

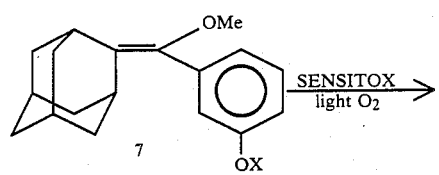

7

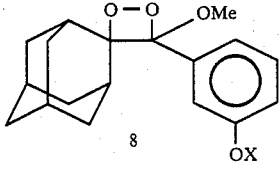

8

(a) X = H
(b) X = Si(t-Bu)Me$_2$

Instrumentation

Nuclear magnetic resonance (NMR) spectra were obtained on either a Nicolet NT300 ™ or a General Electric QE300 ™ spectrometer as solutions in CDCl$_3$ with tetramethylsilane as internal standard unless noted otherwise. Infrared (IR) spectra were obtained on either a Nicolet ™ or a Beckman Acculab 8 ™ spectrometer Mass spectra were obtained on either a Kratos ™ or an AEI MS-90 ™ spectrometer. Ultraviolet and visible absorption spectra were obtained on a Varian Cary 219 ™ spectrophotometer. High performance liquid chromatography (HPLC) was performed with a Varian 5020 LC ™. Fluorescence spectra were recorded on either an Aminco-Bowman ™ or a Spex Fluorolog/ ™ spectrophotofluorometer. Chemiluminescence spectra were measured using either the Spex Fluorometer or a device constructed in this laboratory. Kinetic measurements were made using another device built in this laboratory which is interfaced to an Apple IIe ™ computer. Elemental analyses were performed by Midwest Microlabs, Indianapolis. Melting points were measured in a Thomas Hoover ™ capillary melting apparatus and are uncorrected. Precision weights were obtained on a Cahn model 4700 ™ electrobalance.

Materials

The solvents: o-xylene, toluene, propylene carbonate, N,N-dimethylformamide, N-methylpyrrolidinone, 2-methoxyethanol, 1,2-dimethoxyethane, and nonane were obtained from Burdick and Jackson Laboratories and used as received for kinetic and spectroscope measurements. Methylcyclohexane was purified by passage over neutral alumina and fractional distillation. 1,4-Dioxane was distilled from sodium and then from Na₄EDTA. 9,10-Diphenylanthracene and 9,10-dibromoanthracene were recrystallized from either o-xylene or 2-methoxyethanol. Silica, alumina and the other solid supports were obtained from various commercial sources as noted and used without further purification.

Syntheses of Alkenes 1,6-Dibromo-2-naphthol. A 200 mL three-neck round bottom flask fitted with condenser, addition funnel and gas outlet tube as charged with 2-naphthol (21.6 g, 150 mmol) in 60 mL of glacial acetic acid. A solution of bromine (48 g, 300 mmol) in 15 mL of acetic was added dropwise. On completion the warm solution was heated on a steam bath for 90 minutes. A solution of KOH in water was used to scrub the HBr evolved through the outlet during the heating. On standing overnight at room temperature the product crystallized. The contents were cooled to 0° C. and filtered with suction. The light brown product weighed 41.5 g (92%) after air drying and was sufficiently pure for use in the next step.

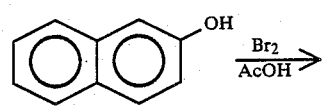

6-Bromo-2-naphthol. To a solution of 225 mL of ethanol and 90 mL of conc. HCl in a 500 mL round bottom flask were added of tin metal (32.6 g, 274 mmol) and 1,6-dibromo-2-naphthol (41.5 g, 137 mmol). The reaction mixture was refluxed on a steam bath for 9 hours. TLC (SiO₂, 15:1 benzene/ethyl acetate) indicated consumption of starting material. The cooled solution was decanted from unreacted tin, concentrated to 150-200 mL on vacuo and poured into 600 mL of ice and water The white precipitate was collected on a Buchner funnel and dried in the air to afford 31.5 g of an off-white solid. Recrystallization from benzene produced 23.8 g of pure product (78%): mp 127°-127.5° C.; lit. mp 127°-129° C.; reference: C. R. Koelsch, Org. Syn. Coll. Vol. 3, 132 (1955).

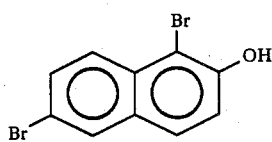

6-Hydroxy-2-naphthoic acid A 500 mL three-neck flask fitted with magnetic stirrer, nitrogen lines and a 125 mL addition funnel was charged with 200 mL of dry ether (newly opened can) and 6-bromo-2-naphthol (15.6 g, 70 mmol) The atmosphere was replaced with nitrogen and a solution of 15 mL of 10M n-BuLi in 100 mL of ether (150 mmol) was added via the addition funnel over a 30 minute period. The solution became pale yellow with a precipitate. After stirring for 20 minutes more, dry ice was added until the solution became quite cold (<−25° C.) and green in color The solution was warmed to room temperature and quenched by the addition of 200 mL of water. The two-phase system was transferred to a separatory funnel, the layers separated and the ether solution extracted with 100 mL of saturated NaHCO₃ solution. The combined aqueous layers were washed with 100 mL of ether and neutralized by careful addition of 12N HCl. The pale blue solid was filtered and dried in the air to give 10.3 g (76%): mp 238°-241° C. (dec.); lit. mp 240°-241° C.; reference: S. V. Sunthankar and H. Gilman, J. Org. Chem., 16, 8 (1951).

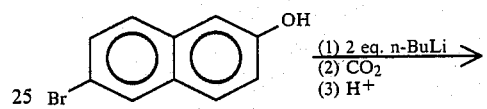

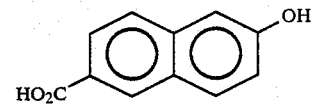

Methyl 6-hydroxy-2-naphthoate. 6-Hydroxy-2-naphthoic acid (5.0 g, 26.6 mmol) was dissolved in 125 mL of methanol and refluxed with 6 drops of conc. H₂SO₄ for 36 hours. TLC analysis (SiO₂, 10:1 CHCl₃/MeOH) revealed only a trace of the acid left. The solution was cooled partially and concentrated to dryness on a rotary evaporator. The solid residue was dissolved in 200 mL of ether and washed successively with 100 mL of saturated aq. NaHCO₃ and brine Drying over MgSO₄ and evaporating the solvent left 4.6 g of (85.5%) slightly yellow solid which showed only one spot on TLC. The material is sufficiently pure for use in subsequent reactions but may be purified solid mp 169°-169.5° C.; ¹H NMR delta 3.976 (s, 3H), 5.3 (br s, 1H), 7.16-8.54 (m, 6H); IR (KBr) 3370, 1680, 1630, 1435, 1310, 1210 cm⁻¹.

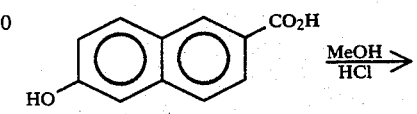

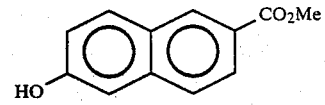

Methyl 6-tert-butyldimethylsilyloxy-2-naphthoate. A 10 mL round bottom flask fitted with magnetic stirrer and pressure-equalizing dropping funnel was charged with 3 mL of DMF which had been dried by vacuum distillation from CaH₂. Methyl 6-hydroxy-2-naphthoate (1.01 g, 5 mmol) and t-butyldimethyl silyl chloride (0.83 g, 5.5 mmol) were added and the atmosphere replaced with nitrogen. A solution of imidazole (0.75 g, 11 mmol) in 3 mL of dry DMF was added via the dropping funnel

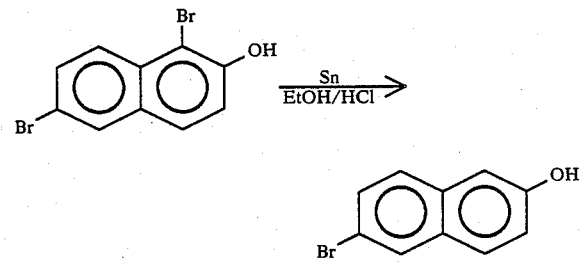

over 15 minutes, and stirring continued for 4 hours TLC analysis (SiO$_2$, 5% ethyl acetate/hexane) showed clean conversion to a new material. The solution was poured into 50 mL of 1% aq. Na$_2$CO$_3$ solution and extracted with 3-35 mL portions of pentane. The combined pentane solutions were washed with 25 mL of water, 25 mL of brine and dried over MgSO$_4$. Evaporation of the pentane yielded 1.45 g of slightly yellow solid. Purification by column chromatography on silica using 5% (V/V) ethyl acetate/hexane as eluent afforded 1.4 g (88%) of white solid after recrystallization from pentane mp 72°-72.5° C.; $^1$H NMR delta 0.266 (s, 6H), 1.022 (s, 9H), 3.958 (s, 3H), 7.19-8.53 (m, 6H); $^{13}$C NMR delta −4.35, 18.23, 25.64, 52,03, 114 74, 122 87, 125 38, 125.62, 126.75, 128.16, 130.87, 130.95, 137.10, 155.69, 167.36; IR (KBr) 2950, 2860, 1715, 1635, 1605, 1480, 1290, 1210 cm$^{-1}$; MS m/e (rel. intensity) 316 (33, 285(7), 260 (33), 259 (100), 200 (11), 185 (13), 141 (8).

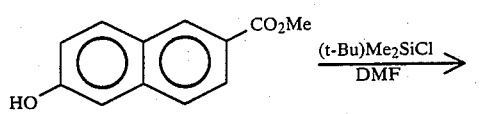

Methyl 6-tert-butyldiphenylsilyloxy-2-naphthoate. A 10 mL round bottom flask equipped with magnetic stirrer and pressure-equalizing addition funnel was charged with 3 mL of dry DMF, Methyl 6-hydroxy-2-naphthoate (1.01 g, 5 mmol) and tert-butyldiphenylsilyl chloride (1.51 g, 5.5 mmol). The atmosphere was replaced with nitrogen and a solution of imidazole (0.75 g, 11 mmol) in 3 mL of dry DMF was added dropwise over a 15 minute period Stirring was continued for 5 hours. The solution was added to 25 mL of water and extracted 3 times with 25 mL portions of pentane. The combined pentane solutions were washed with 25 mL of brine and stored at −25° C. The crystals were collected and a second crop obtained by concentrating the mother liquor to 5 to 10 mL and cooling to −25° C. This process afforded 1.98 g (90%) of colorless crystals mp 86°-87° C.; $^1$H NMR delta 1.139 (s, 9H), 3.919 (s, 3H), 7.1-8.5 (m, 16H); $^{13}$C NMR delta 19.46, 26.47, 51.99, 114.62, 122.43, 125.46, 126.81, 127.87, 130.07, 130.73, 130 77, 132.51, 135.46, 155.52, 167.33; IR (KBr) 3020, 2925, 2860, 1715, 1630, 1600, 1480, 1270, 1200, 690 cm$^{-1}$.

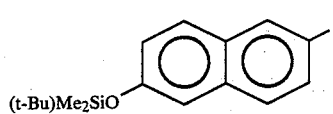

(6-tert-Butyldimethylsilyloxy-2-naphthyl)methoxymethlene]adamantane (1c). A 250 mL three-neck flask was fitted with a reflux condenser 125 mL addition funnel, CaCl$_2$ drying tube and nitrogen line. The apparatus was dried by means of a hot air gun and nitrogen purging THF (150 mL) distilled from Na/benzophenone was added and the flask cooled in an ice-water bath Titanium trichloride (12 g, 78 mmol) was added rapidly (fumes in air!) followed by lithium aluminum hydride (1.425 g, 37.5 mmol) in portions with vigorous stirring. The cooling bath was removed and the black mixture was allowed to warm to room temperature. Triethylamine (6 mL, 43 mmol) was added dropwise to the stirred suspension and reflux begun. After 1 hour at reflux, a solution of methyl 6-tert-butyldimethylsilyloxy-2-naphthoate (2.38 g, 7.5 mmol) and adamantanone (1.15 g, 7.67 mmol) in 50 mL of dry THF was added dropwise to the refluxing mixture over an 18 hour period. Reflux was continued for an additional 6 hours. The cooled reaction mixture was quenched by careful addition of 10 mL of methanol and 10 mL of water. The mixture was diluted with 50 mL of pentance and passed down a column of florisil (4″×1.5″), eluting with pentane, then 1:1 ether/pentane. If any of the black material passes through the column it may be removed by extracting the organic phase with water The pooled organic solutions were concentrated on a rotary evaporator producing a yellow oil which was chromatographed on silica with 5% (V/V) ethyl acetate/hexane. The product containing fractions when evaporated left 1.8 g of a yellow oil which afforded 1.27 g of 1c as slightly yellow crystals from cold pentane: mp 97.5°-98° C.; $^1$H NMR delta 0.250 (s, 6H), 1.024 (s, 9H), 1.80-1.99 (m, 13H), 2.697 (s, 1H), 3.321 (s, 3H), 7.05-7.72 (m, 6H); $^{13}$C NMR delta −4.34, 18.27, 25.73, 28.39, 30.28, 32.32, 37.25, 39.13, 39.28, 57.76, 114.78, 122.19, 126.32, 127.74, 128,06, 128.86, 129.44, 130.88, 131.56, 134.00, 143 73, 153 70; MS m/e (rel. intensity) 435 (37, M +1), 434 (100), 377 (18), 345 (5), 188 (6), 162 (18), 14 (11), 73 (20). IR (KBr) 2940, 2915, 1630, 1600, 1480, 1265, 1250, 1090, 855, 840 cm$^{-1}$.

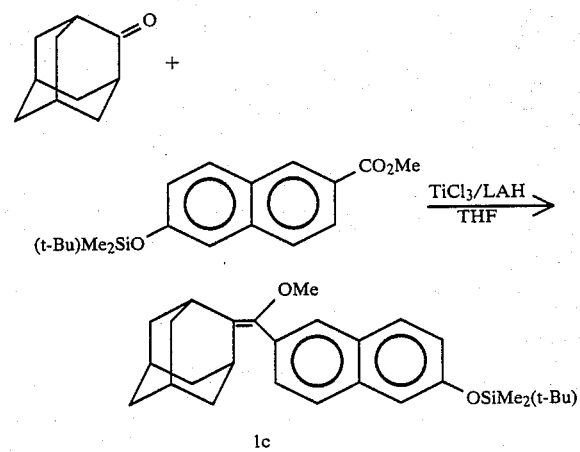

[(6-tert-Butyldiphenylsilyloxy-2-naphthyl)methoxymethylene]adamantane 1d). Approximately 7 g of a 2:1 mixture of TiCl$_3$ and lithium aluminum hydride (Aldrich) was cautiously added to a 250 mL dry three-neck round bottom flask containing 150 mL of dry THF maintained at 0° C. by an ice bath. The resulting black mixture was stirred at 0° C. for 10 minutes and triethylamine (3.3 mL, 24 mmol) was added. The mixture was refluxed for 1 hour and a solution of methyl tert-butyldiphenylsilylnaphthoate (1.76 g, 4 mmol) and adamantanone (600 mg, 4 mmol) in 40 mL of dry THF was added over 6 hours. Reflux was continued for an additional 4 hours and the mixture cooled to room temperature.

The reaction mixture was quenched by dropwise addition of 5 mL of methanol followed by 10 mL of water. The THF solution was decanted from the viscous black residue and concentrated to under 50 mL. This solution was diluted with ether and passed down a column of Florisil eluting first with pentane then with 1:1 ether/pentane. Evaporation of solvent left 1.9 g of a yellow oil. This oil was dissolved in hexane, filtered and chromatographed with 3% ethyl acetate/hexane on silica affording 900 mg of a pale yellow oil which is homogeneous by TLC and NMR; $^1$H NMR delta 1.133 (s, 9H), 1.75–2.0 (m, 13H), 2.65 (s, 1H), 3.283 (s, 3H), 7.00–7.85 (m, 16H); $^{13}$C NMR delta 19.49, 26.54, 28.35, 30.24, 32.29, 37.23, 39.09, 57.73, 114.42, 121.67, 126.35, 127.59, 127.83, 127.94, 128.61, 129.22, 129.95, 130.76, 131.51, 132.87, 133.76, 135.52, 143.67, 153.55; MS m/e (rel. intensity) 558 (68), 502 (43), 501 (100), 250 (14), 222 (11), 176 (19), 162 (25), 135 (11), 105 (22).

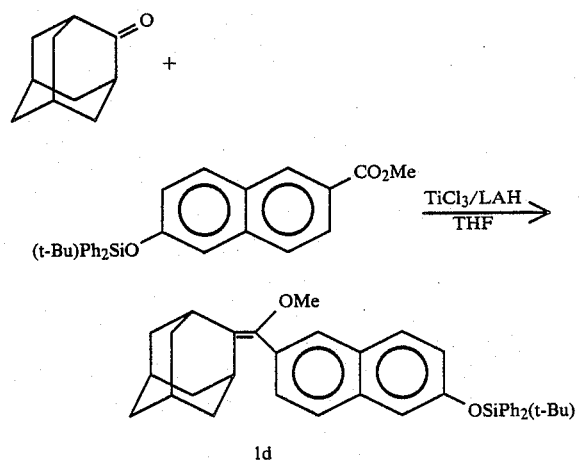

[(6-Hydroxy-2-naphthyl)methoxymethylene]adamantane (1b). To a stirred solution of the tert-butyldimethylsilyl protected alkene 1c (276 mg, 0.635 mmol) in 10 mL of THF were added 0.65 mL of a 1.0M solution of tetra-n-butylammonium fluoride trihydrate in THF. The solution which instantly became bright yellow was stirred for one hour and then poured into a separatory funnel containing 100 mL of ether and 100 mL of water. The layers were separated and the aqueous layer extracted with another 25 mL of ether. The combined ether solutions were dried with MgSO$_4$ and evaporated to yield an amber oil which was chromatographed on SiO$_2$ using 15–25% ethyl acetate/hexane. There resulted 195 mg (96%) of white solid; mp 143°–4° C.; $^1$H NMR delta 1.8–2.1 (m, 13H), 2.697 (s, 1H), 3.336 (s, 3H), 5.25 (s, 1H OH exchange with D$_2$O), 7.08–7.76 (m, 6H); $^{13}$C NMR delta 28.37, 30.31, 32.36, 37.24, 39.12, 39.27, 57.80, 109.39, 117.89, 126.06, 128.14, 128.46, 129.59, 130.48, 132.01, 134.03, 143.47, 153.66; IR (KBr) 3290, 2890, 2840, 1630, 1610, 1280, 1195, 1180, 1070, 860 cm$^{-1}$; MS m/e (rel. intensity) 320 (100), 263 (15), 171 (50), 143 (13), 115 (10).

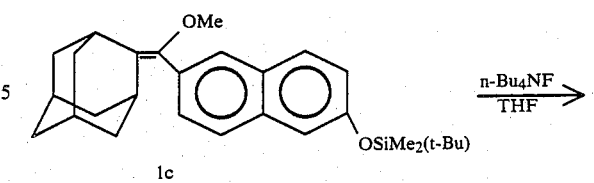

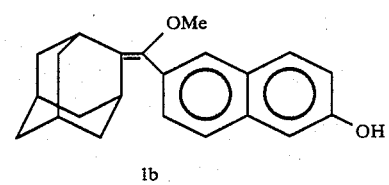

6-Acetoxy-2-naphthyl)methoxymethylene]adamantane (1e). The corresponding hydroxy alkene 1b (96 mg, 0.3 mmol) was dissolved in 10 mL of CH$_2$Cl$_{12}$ and pyridine (244 mg, 3 mmol) under N$_2$. The solution was cooled in an ice bath and a solution of acetyl chloride (98 mg, 1.25 mmol) in 1 mL of CH$_2$Cl$_2$ was added dropwise via syringe. A white precipitate formed. After two hours at 0°–5° C. TLC (SiO$_2$, 3:1 hexane/ethyl acetate) showed complete acetylation. After removal of the solvent in vacuo the solid residue was washed with 30 mL of ether. The ether was washed with 3×25 mL of water, dried over MgSO$_4$ and evaporated to dryness. The oily product was chromatographed on silica using 4:1 hexane/ethyl acetate as eluent affording 70 mg (64%) of 1e as a white solid: $^1$H NMR delta 1.8–2.1 (m, 13H), 2.347 (s, 3H), 2 (s, 1H), 3.315 (s, 3H), 7.21–7.85 (m, 6H); $^{13}$C NMR delta 21.08, 28.33, 30.77, 32.35, 37.19, 39.09, 39.23, 57.77, 110.34, 121.28, 127.32, 128.11, 129.48, 131.15; IR (KBr) MS (70 eV), m/e 362 (100), 320 (92), 263 (21), 171 (30).

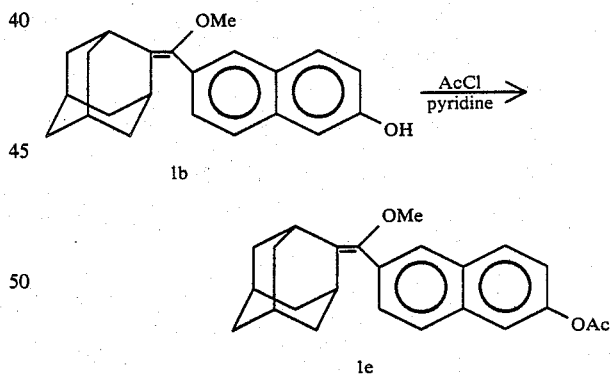

2-tert-Butyldimethylsilyloxy-9H-fluoren-9-one. The procedure for this reaction was the same as described above for methyl 6-tert-butyldimethylsilyloxy-2-naphthoate. A solution of imidazole (0.5 g, 7.4 mmol) in 2 mL of dry DMF was added to a solution of 2-hydroxy-9-fluorenone (Aldrich, 0.55 g, 2.8 mmol) and tert-butyldimethylsilyl chloride (0.5 g, 3.3 mmol) in 5 ML of dry DMF to give after workup 0.74 g (84%) of a yellow oil: $^1$H NMR (CDCl$_3$) delta 7.612–6.891 (m, 7H), 0.994 (s, 9H), 0.224 (s, 6H); $^{13}$C NMR (CDCl$_3$ delta 193.69, 157.04, 144.87, 137.52, 136.04, 134.73, 134.50, 127.92, 125.59, 124.28, 121.24, 119.56, 116.22, 25.60, 18.18, −4.46.

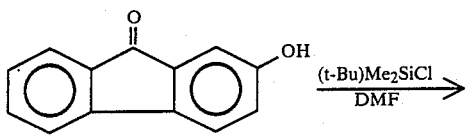

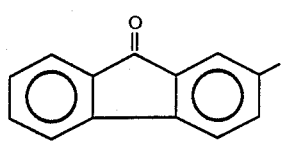

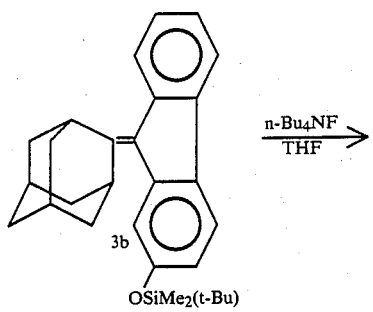
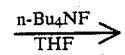

2-tert-Butyldimethylsilyloxy-9H-fluoren-9-ylideneadamantane (3b). A solution of 2-tert-butyldimethylsilyloxy-9H-fluoren-9-one (0.689 g, 2.2 mmol) and adamantanone (0.66 g, 4.4 mmol) in 30 mL of dry THF was added dropwise over a period of 7 h to a refluxing mixture of TiCl$_3$ (6.8 g, 44 mmol), LAH (0.8 g, 21 mmol) and triethylamine (3 mL) in 80 mL of dry THF. The reaction was refluxed for an additional 12 h. The alkene was then isolated and purified as described above for 1a to give 0.65 g (68%) of 3b: mp 102°–105° C.; $^1$H NMR (CDCl$_3$) delta 7.832–6.785 (m, 7H), 4.038 (s, 1H), 3.972 (s, 1H), 2.095–1.990 (m, 12H), 1.006 (s, 9H), 0.225 (s, 6H); $^{13}$C NMR (CDCl$_3$) delta 159.91, 155.06, 140.64, 139.89, 139.13, 33.61, 126.29, 125.65, 124.31, 119.87, 118.71, 118.43, 116.35, 39.49, 39.40, 36.90, 35.99, 35.90, 27.83, 25.81, 25.73, 18.35, −4.33.

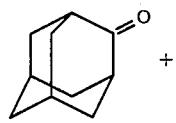

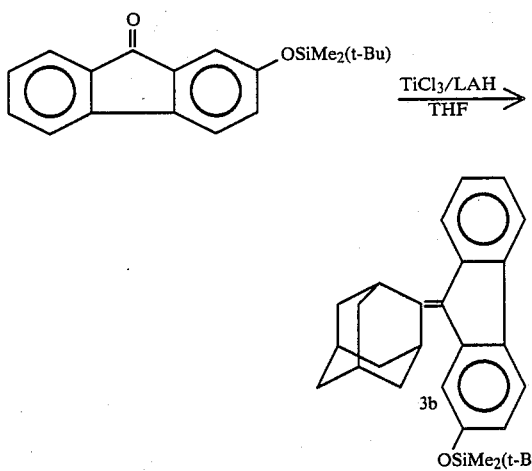

2-Hydroxy-9H-fluoren-9-ylideneadamantane (3a). A solution of n-Bu$_4$NF. 3H$_2$O (1.4 mL, 1.0M) in THF was added to a stirred solution of alkene 3b (0.525 g) in 10 mL of THF. The workup procedure was the same as described above for 1b. The yield of 3a was 0.27 g (71%): $^1$H NMR (CDCl$_3$) δ7.838–6.760 (m, 7H), 4.878 (s, 1H, OH), 4.043 (s, 1H), 3.975 (s, 1H), 2.079–1.977 (m, 12H); $^{13}$C NMR (CDCl$_3$) δ 154.84, 140.96, 139.68, 138.97, 133.33, 126.29, 125.67, 124.34, 120.09, 118.61, 113.61, 111.73, 39.45, 36.78, 35.90, 35.79, 27.72.

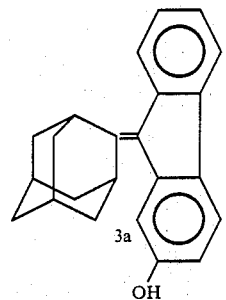

3-Hydroxy-9H-xanthen-9-one. Resorcinol (5.5 g, 50 mmol) and methyl salicylate (11.0 g, 72 mmol) were refluxed for 5 h using a Dean-Stark trap to remove H$_2$O and MeOH. The resulting black oil was chromatographed over silica with 20% ethyl acetate-hexane as eluent. A yellow solid was isolated which was subsequently recrystallized from ethyl acetate to give 1.3 g (12.3%) of 3-hydroxy-9H-xanthen-9-one (lit. mp 242° C.). Literature references to the synthesis of this compound: R. J. Patolia and K. N. Trivedi, *Indian J. Chem.*, 22B, 444 (1983); J. S. H. Davies, F. Scheinmann, and H. Suschitzky, *J. Org. Chem.*, 23, 307 (1958).

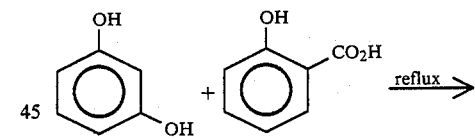

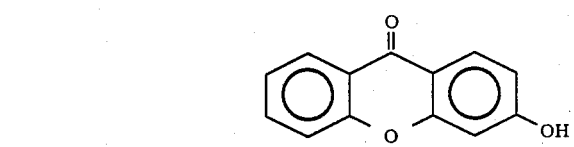

3-(tert-Butyldimethylsilyloxy)-9H-xanthen-9-one. 3-Hydroxy-9H-xanthen-9-one (2.00 g, 9.4 mmol) and tert-butyldimethylsilyl chloride (1.57 g, 10.4 mmol) were dissolved in 20 mL of dry DMF and stirred at room temperature. Imidazole (1.46 g, 21.5 mmol) was added cautiously and the solution was stirred for 4 h. The solution was then transferred to a separatory funnel and 100 mL of hexane was added. After washing with 3-100 mL portions of H$_2$O, the organic layer was dried with MgSO$_4$ and concentrated. Chromatography over silica with 5% ethyl acetate-hexane gave 2.46 g (7.5 mmol, 80.0%) of the protected alcohol as a white solid: mp 79°–81° C.:$^1$H NMR (CDCl$_3$) delta 0.296 (s, 6H), 1.019 (s, 9H), 6.85–6.89 (m, 2H), 7.353 (ddd, 1H, J=8.0, 7.0, 1.0 Hz), 7.441 (ddd, 1H, J=8.5, 1.0, 0.3 Hz), 7.680 (ddd, 1H, J=8.5, 7.0, 1.7 Hz), 8.233 (m, 1H), 8.323 (ddd, 1H, J=8.0, 1.7, 0.3 Hz); $^{13}$C NMR (CDCl$_3$ delta 176.31, 161.78, 157.75, 156.23, 134.25, 128.30, 126.65, 123.75, 121.93, 117.75, 117.67, 116.46, 107.43, 25.51, 18.22, −4.39.

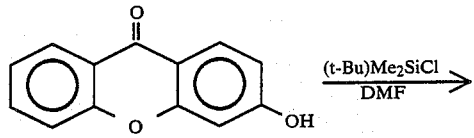

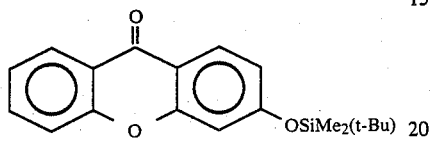

3-(tert-Butyldimethylsilyloxy)-9H-xanthen-9-ylideneadamantane (5b). TiCl$_3$ (12.0 g, 77.8 mmol) was stirred in 100 mL of dry THF at 0° C. LAH (1.56 g, 41.1 mmol) was added cautiously and the black solution was refluxed for 1 h. A solution of the silyloxy xanthone (2.16 g, 6.6 mmol) and 2-adamantanone (2.95 g, 19.7 mmol) in 50 mL of THF was added over 4 h to the TiCl$_3$-LAH solution. The resulting mixture was refluxed for 24 h. The reaction was cooled to 0° C. and MeOH (10 mL) was added. The solution was diluted with H$_2$O (200 mL) and extracted with 2-200 mL portions of hexane. The organic fraction was washed with H$_2$O (400 mL), dried with MgSO$_4$, and concentrated. Chromatography over silica with hexane gave 1.52 g (3.4 mmol, 51.5%) of 5b as a white solid: mp 137.138° C.; $^1$H NMR (CDCl$_3$) delta 0.214 (s, 6H), 0.985 (s, 9H), 1.85-2.07 (m, 12H), 3.45-3.55 (m, 2H), 6.585 (dd, 1H, J=8.4, 2.4 Hz), 6.681 (d, 1H, J=2.4 Hz), 7.04-7.30 (m, 5H); $^{13}$C NMR (CDCl$_3$) delta 155.86, 154.77, 145.36, 127.77, 127.50, 127.05, 126.74, 122.50, 120,05, 117.42, 116.44, 116.12, 114.57, 108.13, 39.50, 39.45, 37.10, 32.60, 32.55, 27.96, 25.66, 18.18, −4.41; HRMS calcd 444.2484, found 444.2480; MS m/e (rel intensity) 444 (100), 443 (31), 387 (25), 253 (9); Anal. calcd for C$_{29}$H$_{36}$O$_2$Si: C, 78.38; H, 8.11. Found: C, 78.70; H, 8.23.

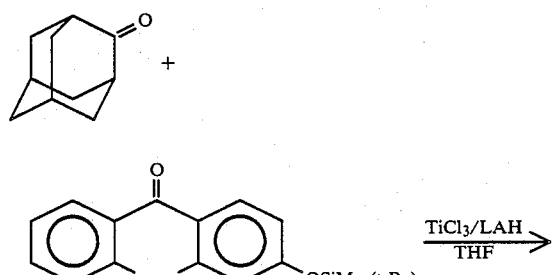

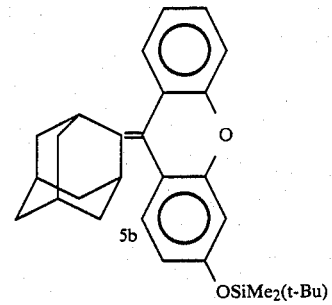

3-Hydroxy-9H-xanthen-9-ylideneadamantane (5a). The silylated alkene 5b (1.18 g, 2.6 mmol) was dissolved in 10 ml of THF. n-Bu$_4$NF.3H$_2$O (0.94 g, 3.0 mmol) was added and the yellow solution stirred for 30 min. The solution was then diluted with Et$_2$O (100 mL), washed with H$_2$O (200 mL), and the organic layer was concentrated. Recrystallization from ethyl acetate gave 0.48 g (1.5 mmol, 57.7%) of 5a as a white solid: 235°-240° C. (dec); $^1$H NMR (CDCl$_3$) delta 1.873 (2, 10H), 1.992 (s, 2H), 3.472 (s, 1H), 3.529 (s, 1H), 6.70-6.76 (m, 2H), 6.96-7.04 (m, 2H), 7.06-7.14 (m, 2H), 7.21-7.29 (m, 2H); HRMS calc. 330.1621, found 330.1617; MS m/e (rel. intensity) 330 (100), 329 (43), 273 (37), 235 (16), 197 (11), 142 (65). Anal. calcd for C$_{23}$H$_{22}$O$_2$: C, 83.64; H, 6.67. Found; C, 83.75; H, 6.69.

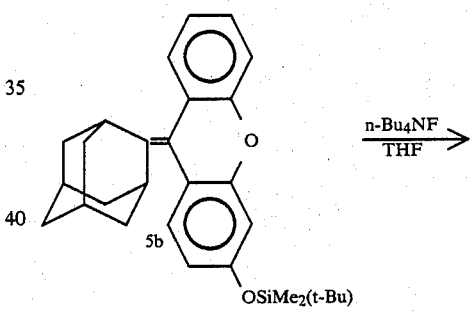

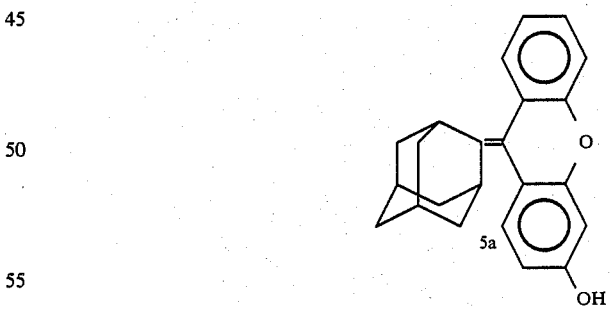

3-Acetoxy-9H-xanthen-9-ylideneadamantane (5c). Hydroxy alkene 5a (0.577 g, 1.5 mmol) was dissolved in 20 mL of CH$_2$Cl$_2$ with 1.25 mL (1.22 g, 15.5 mmol) of pyridine. Acetyl chloride (0.6 mL, 0.662 g, 8.4 mmol) was dissolved in 5 mL of CH$_2$Cl$_2$ and added dropwise to the solution with 5a. A precipitate formed immediately. After stirring for 2 hours, the solvent was removed to give a yellow-orange solid. This material was treated with 50 mL of CH$_2$Cl$_2$ to leave a white solid which was separated by filtration. The CH$_2$Cl$_2$ solution was then concentrated and chromatographed over silica with 5% ethyl acetate/hexane to give 0.502 g (77.2%) of 5c as a white solid: mp 162°-163° C.; ¹H NMR (CDCl₃ delta 1.80-2.05 (m, 12H), 2.265 (s, 3H), 3.45-3.55 (m, 2H), 6.833 (dd, 1H, J=8.38, 2.32 Hz), 6.961 (d, 1H, J=2.33 Hz), 7.072 (ddd, 1H, J=8.11, 5.45, 2.08 Hz), 7.12-7.28 (m, 4H); ¹³C NMR (CDCl₃) delta 20.96, 27.78, 32.50, 36.88, 39.36, 110.08, 115.72, 116.41, 122.75, 124.38, 126.44, 126.90, 127.42, 127.68, 146.81, 149.24, 154.86, 155.48, 169.18.

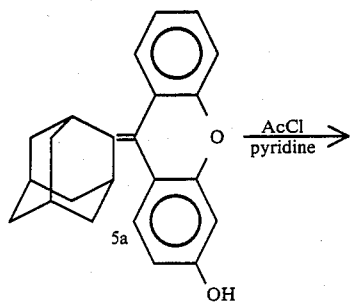

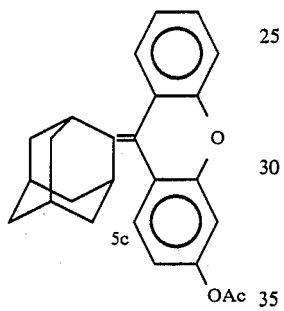

3-Phosphate-9H-xanthen-9-ylideneadamantane, bis(-tetraethylammonium}salt (5d). Phosphoryl chloride (72.98 mg, 0.48 mmol) was dissolved in dry pyridine (3 mL) and stirred at 0° C. The hydroxy alkene 5a (66.35 mg, 0.20 mmol) was dissolved in dry pyridine (5 mL) and added slowly to the phosphoryl chloride/pyridine solution. The resulting solution was stirred at room temperature for 1 h. A 40% solution of Et₄NOH in H₂O (4 mL) was then added slowly after which the pH of the reaction solution was found to be approximately 8. The solution was extracted with CH₂Cl₂ (100 mL), the organic layer subsequently washed with 2-50 mL portions of aqueous KCl (saturated). The organic layer was dried with anhydrous MgSO₄ and concentrated to give 5d as a yellow oil (29.11 mg, 22.3%): ¹H NMR (CDCl₃ delta 1.007 (t, 24H, J=7.24 Hz), 1.70-2.00 (m, 12H), 2.85-2.95 (m, 2H), 3.30-3.45 (m, 16H), 7.00-7.20 (m, 3H), 7.25-7.40 (m, 2H), 7.65-7.75 (m, 1H), 8.55-8.70 (m, 1H).

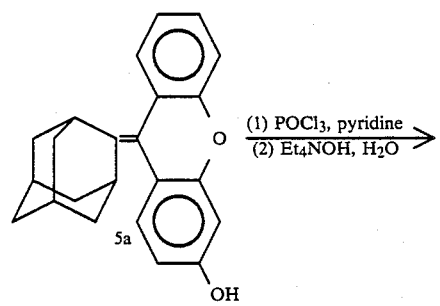

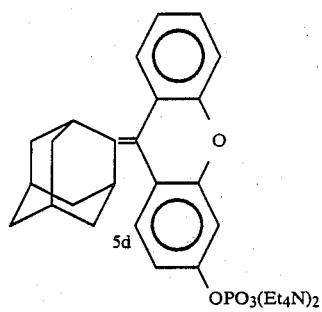

Methyl 3-hydroxybenzoate. m-Hydroxybenzoic acid (10 g, 72.5 mmol) was dissolved in 100 mL of methanol and the solution refluxed with a catalytic amount of HCl. After 24 hours tlc analysis on silica with 10% ethyl acetate/hexane revealed a trace of the starting benzoic acid remaining. The solution was cooled and concentrated to dryness. The solid residue was dissolved in 200 mL of ether and washed with 100 mL of saturated aq. NaHCO₃ and brine. Drying the solution over MgSO₄ and evaporating the solvent left a slightly yellow solid that was purified by recrystallization from benzene/cyclohexane to give methyl 3-hydroxybenzoate as a white solid (6.74 g, 61%): 71°-73° C.

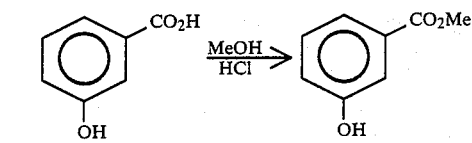

Methyl 3-tert-butyldimethylsilyloxybenzoate. A 50 mL round-bottom flask fitted with a magnetic stirrer and pressure-equalizing dropping funnel was charged with 10 mL of DMF (dried by distillation from CaH₂). Methyl 3-hydroxybenzoate (2.37 g, 16 mmol) and tert-butyldimethylsilyl chloride (3.05 g, 22 mmol) in 10 mL of dry DMF were added and the atmosphere replaced with nitrogen. A solution of imidazole (2.23 g, 33 mmol) in 10 mL of dry DMF was added over 5 min and the stirring continued for 16 hours at room temperature. TLC analysis over silica with 20% ethyl acetate/hexane showed clean conversion to a new material. The reaction solution was transferred to a separatory funnel containing 25 mL of pentane and 25 mL of water. The pentane layer was removed and the aqueous phase extracted with 2-25 mL portions of pentane. The combined pentane fractions were washed with 25 mL of brine and dried with MgSO₄. Evaporation of the pentane gave the silylated alcohol as a slightly yellow oil (4.24 g, 100%).

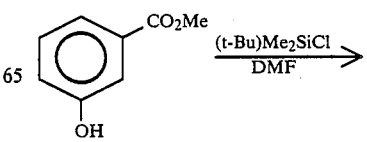

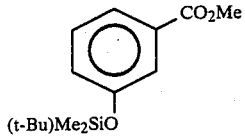

[(3-tert-butyldimethylsilyloxyphenyl)methoxymethylene]adamantane (7b). A 500 mL three-neck flask was fitted with a reflux condenser, 125 mL addition funnel, and nitrogen line. The apparatus was dried by means of a hot air gun and nitrogen purging. Dry THF (200 mL) was added and the flask cooled in an ice bath. TiCL$_3$ (24 g, 156 mmol) was added rapidly followed by LAH (2.8 g, 75 mmol) in portions with stirring. The cooling bath was removed and the black mixture was allowed to warm to room temperature. Triethylamine (12 mL, 86 mmol) was added to the stirred suspension and refluxed for 1 hour. After this period a solution of methyl 3-tert-butyldimethylsilyloxybenzoate (4.40 g, 16.6 mmol) and 2-adamantanone (3.0 g, 20.4 mmol) in 50 mL of dry THF was added dropwise to the refluxing mixture over 5 hours. Refluxing was continued for an additional 4 hours after which the reaction was cooled to room temperature and diluted with 100 mL of ether. The organic solution was separated and concentrated. Chromatography over silica with 1% ethyl acetate/hexane gave 1.29 g (21%) of 7b as an oil: $^1$H NMR (CDCl$_3$) delta 0.196 (s, 6H), 0.985 (s, 9H), 1.78–1.97 (m, 12H), 2.628 (s, 1H, 3.23 (s, 1H), 3.29 (s, 3H), 6.75–7.20 (m, 4H); $^{13}$C NMR (CDCl$_3$) delta −4.50, 18.19, 25.67, 28.37, 30.16, 32.28, 37.25, 38.19, 39.01, 57.51, 119.29, 121.08, 122.32, 128.87, 131.11, 136.84, 143.47, 155.37.

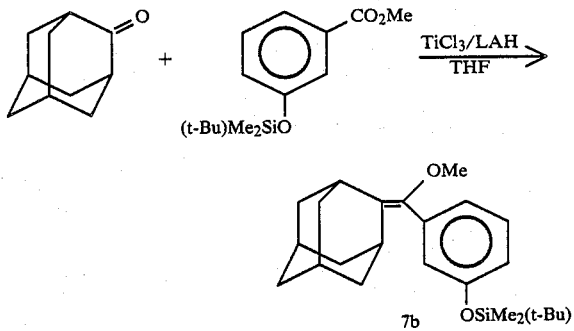

PREPARATION OF 1,2-DIOXETANES

Photooxygenation procedure. Typically a 5–10 mg sample of the alkene was dissolved in 5 mL of CH$_2$Cl$_2$ in the photooxygenation tube. Approximately 40 mg of polystyrene-bound Rose Bengal (Sensitox I) was added and an oxygen bubbler connected. Oxygen was passed slowly through the solution for 5 minutes and the apparatus immersed in a half-silvered Dewar flask containing Dry Ice/2-propanol. The sample was irradiated with either a 250 W or 1000 W sodium lamp (GE LUcalox) and a UV cutoff filter while oxygen was bubbled continuously. Progress of the reaction was monitored by TLC. A spot for the highly stable dioxetanes could usually be detected and had a R$_f$ slightly less than that of the alkene. The unstable dioxetanes decomposed during TLC so the reaction was judged complete when the alkene was completely consumed. For the unstable dioxetanes, the sensitizer was filtered off at −78° C. by using a stream of nitrogen to push the solution through a Dry Ice-jacketed sintered glass funnel and the solution stored at −78° C. This solution was generally used directly for kinetic measurements. The stable adamantyl-substituted dioxetanes were filtered at room temperature, evaporated on a rotary evaporator and recrystallized from a suitable solvent.

4-Methoxy-4-(2-naphthyl)spiro[1,2-dioxetane-3,2'-adamantane](2a). Alkene 1a (125 mg) was photooxygenated in 10 ml of CH$_2$Cl$_2$ at −78° C. with a 1000 W lamp using Sensitox I as sensitizer. TLC analysis (silica gel, 5% ethyl acetate/hexane) showed clean conversion to a more polar material in 80 minutes. Filtration and removal of solvent produced a yellowish oil which crystallized from pentane at −25° C. only after 2 weeks to give 2a: mp 116° C. $^1$H NMR delta 0.9–2.0 (m, 12H), 2.22 (s, 1H), 3.11 (s, 1H), 3.242 (s, 3H), 7.0–8.3 (m, 7H); $^{13}$C NMR delta 25.94, 26.07, 31.60, 31.72, 32.31, 3.08, 33.23, 34.88, 36.42, 50.00, 95.60, 112.33, 125.21, 126.47, 127.02, 127.63, 127.91, 128.67, 129,41, 132.13, 132.85, 133.61.

4-(6-Hydroxy-2-naphthyl)-4-methoxyspiro[1,2-dioxetane-3,2'-adamantane] (2b). The corresponding alkene 1b (18.5 mg) was irradiated with the 1000 W Na lamp in 4 ml of a 1:1 mixture of CH$_2$Cl$_2$ and acetone cooled to −78° C. in the presence of 40 mg of Sensitox I. TLC using 10:1 CH$_2$Cl$_2$/MeOH showed clean conversion to a new material. The sensitizer was removed by filtration and the solvent evaporated giving 19 mg of 2b as a white solid: $^1$H NMR delta 0.9–2.0 (s, 12H), 2.2 (s, 1H), 3.093 (s, 1H), 3.241 s, 3H), 7.1–7.9 (m, 6H); $^{13}$C NMR delta 25.91, 26.03, 31.58, 31.68, 32.33, 33.02, 33.22, 34.84, 36.40, 49.99, 95.77, 109.37, 118.35, 126.39, 128.22, 129.74, 130.67, 134.95, 154.55.

4-(6-tert-Butyldimethylsilyloxy-2-naphthyl)-4-methoxyspiro] 1,2-dioxetane-3,2'-adamantane] (2c). Alkene 1c (30 mg) was photooxygenated in 10 ml of CH$_2$Cl$_2$ at −78° C. with a 1000 W lamp using Sensitox I as sensitizer. TLC analysis (silica gel, 5% ethyl acetate/hexane) showed clean conversion to a more polar material in 60 minutes. Filtration and removal of solvent produced 2c as an oil which crystallized from hexane at −25° C.; mp 107° C.; $^1$H NMR delta 0.268 (s, 6H), 1.030 (s, 9H), 1.4–2.0 (m, 12H), 2.2 (s, 1H), 3.1 (s, 1H), 3.234 (s, 3H), 7.1–7.85 (m, 6H); $^{13}$C NMR delta −4.33, 18.23, 25.67, 25.93, 26.06, 31.59, 31.69, 32.31, 33.04, 33.19, 34.86, 36.42, 49.94, 95.59, 112.44, 114.63, 122.58, 126.64, 128.50, 129.85, 130.11, 134.93, 154.59.

4-(6-Acetoxy-2-naphthyl)-4-methoxyspiro[1,2-dioxetane-3,2'-adamantane] (2e). Alkene 1e (14 mg) was photooxygenated in 4 ml of CH$_2$Cl$_2$ at −78° C. with a 1000 W lamp using 40 mg of Sensitox I as sensitizer. TLC analysis (silica gel, 25% ethyl acetate/hexane) showed clean conversion to a more polar material in 20 minutes. The sensitizer was removed by filtration and the solution diluted to 10.0 mL with dry methylene chloride to make a stock solution whose concentration was ca. 3.8×10$^{-3}$M. An aliquot injected into 3 mL of o-xylene at 95° C. produced chemiluminescence which persisted for several hours.

Dispiro[adamantane-2,3'-[1,2]dioxetane-4',9''-(2-tert-butyl dimethylsilyloxy-9-fluorene)] (4b). Alkene 3b (100 mg) was photooxygenated in CH$_2$Cl$_2$ (5 mL) containing 80 mg of Sensitox I for 4 hours. Dioxetane 4b was subsequently purified by preparative tlc on silica gel using 5% ethyl acetate/hexane: $^1$H NMR (CDCl$_3$) delta 0.233 (s, 6H), 1.016 (s, 9H), 1.257–1.998 (m, 12H), 3.022 (bs, 2H), 6.860–7.988 (m, 7H); $^{13}$C NMR (CDCl$_3$) delta −4.44, −4.38, 18.27, 25.48, 25.71, 31.85, 33.18, 33.36, 33.62, 33.73, 36.01, 94.42, 97.51, 119.32, 120.82, 121.97, 126.05, 126.68, 130.24, 133.42, 140.17, 142.41, 155.39.

4-(3-tert-Butyldimethylsilyloxyphenyl)-4-methoxyspiro[1,2-dioxetane-3,2′-adamantane] (8b). Alkene 7b (98.8 mg) was photooxygenated in 3 mL of CH$_2$Cl$_2$ using Sensitox I. TLC analysis over silica with 10% ethyl acetate/hexane showed clean conversion to a more polar material in 40 min. Filtration and removal of the solvent produced 8b as an oil: $^1$H NMR (CDCl$_3$) delta 0.195 (s, 6H), 0.989 (s, 9H), 1.26–1.90 (m, 13H), 3.023 (s, 1H), 3.231 (s, 3H), 6.86–7.30 (m, 4H).

Dioxetanes 2d, 4a, 6a, 6b, 6c and 7a have been prepared using the above procedures and have been shown to exhibit triggering properties similar to dioxetanes 2a–c and 2e.

Dispiro[adamantane-2,3′-[1,2]dioxetane-4′,9″-(3-phosphate-9H-xanthene] (6d). Alkene 5d (14.6 mg) was photooxygenated in 4 mL of CH$_2$Cl$_2$ at −78° C. with a 1000 W high pressure sodium lamp using 56.3 mg of Sensitox I as sensitizer. The solution was irradiated for 2 h to yield a stock solution of 6d for the enzyme triggering experiments.

CHEMILUMINESCENCE KINETICS PROCEDURES

Rates of dioxetane decomposition were monitored by the decay of chemiluminescence of aerated solutions. A cylindrical Pyrex vial equipped with magnet stir bar was filled with 3–4 mL of the reaction solvent, sealed with a Teflon-lined screw cap and placed in the thermostatted sample block of the chemiluminescence-measuring apparatus (Black Box). Temperature control was provided by an external circulating water bath. Appropriate values for the instrument gain and optical slit size were selected. When thermal equilibrium was reached (ca. 3 min.) an aliquot of the dioxetane stock solution sufficient to achieve a final concentration not greater than 10$^{-4}$M was added via pipette by opening the top of the Black Box or via syringe through a light-tight rubber septum located in the cover directly above the vial. The vial was sealed with a Teflon-lined screw cap to prevent evaporation when high temperatures were used. Measurement of the signal was begun by opening the shutter. The chemiluminescent decay was generally recorded for at least three half-lives. Calculation of the first-order rate constant, k, from the ln(Intensity) vs. time data was performed by a computer program utilizing a standard least-squares treatment. The correlation coefficient, r, was typically at least 0.999 and varied less than 5% between replicate samples. The observed rate was not measurably concentration dependent.

ACTIVATION PARAMETERS FOR DIOXETANE DECOMPOSITION

Activation parameters for decomposition of the dioxetanes were calculated from plots of ln k vs. 1/T (Arrhenius eq.) or ln k/t vs. 1/T (Eyring eq.) by a standard least-squares linear regression analysis. In a typical plot, the result of replicate runs at 5 to 10 temperatures encompassing a 25°–50° C. temperature range were found to yield a straight line with a correlation coefficient of 0.999 or better.

The activation energy for chemiluminescence, $E_{CL}$, was determined for several dioxetanes using the "temperature jump" method of Wilson and Schaap (T. Wilson and A. P. Schaap, J. Amer. Chem. Soc., 93, 4126 (1971)). This method involved measuring the chemiluminescence intensity at one temperature, rapidly changing the temperature (2–3 min) under conditions of constant dioxetane concentration and measuring the new intensity. The activation energy of the light-producing step is given by the relation:

$$E_{CL} = R \, ln(I_1/I_2)/(1/T_2 - 1/T_1)$$

where R is the gas constant. This method has the advantage that it is unaffected by other non-luminescent, possibly catalytic, pathways for dioxetane decomposition which can complicate the determination by the isothermal method. Agreement between the activation energies determined by the two methods indicates that only the "normal" unimolecular mode of decomposition is operative and that catalyzed destruction of the dioxetane by impurities is unimportant.

A third method which combines features of the other two methods was performed by measuring the constant light intensity at several temperatures by making a series of temperature steps. If the dioxetane concentration is unchanged then intensity is proportional to the rate constant, k, and a plot of ln I vs. 1/T has a slope of $-E_{CL}/R$.

Activation Energies for Decomposition of Dioxetanes 2 in Xylene.

| Dioxetane | $E_a$ | log A | k(sec$^{-1}$) at 25° C. | t$_\frac{1}{2}$ at 25° C. |
|---|---|---|---|---|
| 2a | 29.7 | 13.2 | 3.17 × 10$^{-9}$ | 6.9 yrs |
| 2b | 29.7 | 13.3 | 3.83 × 10$^{-9}$ | 5.7 yrs |
| 2c | 27.0 | 11.7 | 8.72 × 10$^{-9}$ | 2.5 yrs |

The above results demonstrate the very high stability (long half-life) that the dioxetanes exhibit before triggering with the appropriate chemical agent or enzyme.

Acquisition of Chemiluminescence Spectra

Spectra of the chemiluminescence emission from dioxetane decomposition were collected by conducting the reaction (either thermal or triggered) in a 1-cm square quartz cuvette in the sample compartment of a Spex Fluorolog spectrofluorometer. The sample holder was thermostatted by means of an external water bath which circulated water/ethylene glycol through the block. A magnetic stirrer mounted below the sample holder assured constant temperature. Correction for the decay of the chemiluminescence intensity during the wavelength scan was made by accumulating the spectrum in a ratio mode whereby the observed spectrum was divided by the signal from an auxiliary detector (EMI 9781B) which measures the total signal as a function of time. The monochromator bandpass was typically 18 nm. For weakly emitting samples, several identical scans were performed and added together to improve the signal-to-noise ratio.

When the chemiluminescence decays were measured at elevated temperatures, the concentration of dioxetane was corrected for the volume expansion of the solvent. Temperature correction plots for all solvents employed were constructed by measuring the change in absorbance with temperature of a dilute solution of DBA at 404 nm or of 1,2-ethanediol-bis-(3-dimethylaminobenzoate) at 347 nm. Plots of % (absorbance at 23° C.) vs. temperature over the range 23° C. to the highest temperature used, usually about 90° C., were found to be linear so that the correction factor (<1) could be interpolated directly from the plot.

PROCEDURES FOR CHEMICAL TRIGGERING OF DIOXETANES

A solution of the dioxetane in a suitable solvent (e.g. o-xylene) was placed in the reaction vial as described above. The vial was placed in the sample holder which was maintained at a temperature such that thermal decomposition of the dioxetane was negligible. Instrument parameters were selected as above and data collection started. A solution of the releasing agent (e.g. base or fluoride) preferably in the reaction solvent was injected by syringe into the rapidly stirred dioxetane solution. The volume of releasing agent added was generally less than 5% of the total volume so that temperature fluctuation of the sample during the time course of the decay was minimal. The pseudo-first order decay was monitored for at least three half-lives.

1. Triggering the Chemiluminescence of Hydroxy-Substituted Dioxetanes with Base: Potassium tert-butoxide induced decomposition of 2b. Treatment of a $10^{-4}$M solution of dioxetane 2b in o-xylene with a solution of potassium t-butoxide in o-xylene (final concentration of base=0.005M) resulted in an intense blue chemiluminescence which decayed with a half-life of approximately 20 seconds at 25° C. Similar experiments with 2b in methanol using KOH as the base or in o-xylene with n-BuLi as the base also resulted in bright blue chemiluminescence with similar decay rates. Base-induced decomposition of dioxetanes 4a, 6a and 8a also produced chemiluminescence at room temperature.

2. Triggering the Chemiluminescence of Silyloxy-Substituted Dioxetanes with Fluoride Ion: Fluoride ion induced decomposition of 2c. An aliquot of a methylene chloride stock solution of dioxetane 2c was injected into 3 mL of 0.01M tetrabutylammonium fluoride in 2-methoxyethanol resulting in a final dioxetane concentration of $10^{-4}$M. Blue chemiluminescence was produced which decayed according to pseudo-first order kinetics with a half-life of about 20 minutes at room temperature. (Dioxetanes 2d, 4b, 6b, and 8b also undergo similar fluoride induced chemiluminescence. These dioxetanes also yield bright chemiluminescence in polar aprotic solvents such as acetonitrile.). The corresponding decomposition of 2c at 25° C. in the absence of fluoride ion exhibits a half-life of 2.5 years. A spectrum of the chemiluminescence obtained from the fluoride triggering of 2c in 1:1 aqueous/2-methoxyethanol is shown in FIG. 1 with the solid line. The fluorescence of the cleavage product (methyl 6-hydroxy-2-naphthoate) from the dioxetane is also shown with the dashed line for comparison. These results demonstrate that it is the singlet excited state of the ester and not adamantanone which gives rise to the observed chemiluminescence.

Enzymatic Triggering of Chemiluminescent Dioxetanes

1. Aryl Esterase

A secondary stock solution of the acetate-protected dioxetane 2e was made by evaporating an aliquot of the methylene chloride stock equivalent to 10 micromoles of dioxetane and dissolving in 5.0 mL of 2-methoxyethanol to give a final concentration of 0.002M. This solution when stored at 0° C. was stable indefinitely. Buffer solutions prepared in distilled water were 0.05M phosphate pH 7.6 and 8.0, 0.02M Tris (tris-hydroxymethylaninomethane maleate) pH 7.6, and pH 9.0 phosphate/borate buffer. Aryl esterase (also called carboxylic ester hydrolase (P-5221)) from porcine liver was purchased from Sigma Chemical Co. as a suspension of 11 mg of protein per mL in 3.2M $(NH_4)_2SO_4$ solution pH 8.0. Each mg of protein is equivalent to 260 Units, where 1 Unit is defined as the amount which will hydrolyze 1 micromole of ethyl butyrate in 1 minute at pH 8.0, 25° C. When a 150 µL (0.3 µmol) aliquot of the acetoxy-dioxetane stock solution was added to 3.0 mL of pH 7.6 Tris buffer at 25 ° C. in the Black Box, no chemiluminescence signal was detected. Injection of 1 µL of (0.26 units) of aryl esterase to the stirred solution caused a chemiluminescent signal to appear. The intensity reached a maximum at about 3 minutes and decayed over a 30 minute period. That this chemiluminescence is due only to an enzyme-catalyzed hydrolysis of the acetate ester function is demonstrated by the following series of experiments:

(1.) Repeating the experiment described above without either the dioxetane or the enzyme produced no chemiluminescence. (2.) Catalysis of the dioxetane decomposition by the medium in which the enzyme is constituted was ruled out since a solution of 150 µL of dioxetane stock in 3 mL of Tris buffer containing 5 µL of 3M $(NH_4)_2SO_4$ produced no chemiluminescence at 25° C. (3.) When distilled water was substituted for the Tris buffer, no chemiluminescence signal was observed, but on adding Tris buffer to this solution light emission similar to that above was produced. (4.) In similar experiments where 150 µL of dioxetane stock in 3 mL of Tris buffer was triggered with 1 µL of enzyme at 25°, 37° and 50° C., the maximum light intensity, $I_{MAX}$, increased with increasing temperature while the rate of decay of light emission and time required to reach maximum intensity, $t_{MAX}$, both decreased. (5.) Denaturing the enzyme by heating 1 µL in 3 mL of Tris buffer to 90° C. and cooling to 25° C. resulted in no chemiluminescence when an aliquot of the dioxetane stock solution was subsequently added. Addition of untreated enzyme preparation to this solution again produced light. 6.) Addition of the known enzyme inhibitor, sodium lauryl sulfate (SDS), to a solution of 3 mL of Tris buffer, 150 µL of dioxetane stock solution and 1.5 µL of enzyme when the light emission had reached a maximum caused an irreversible decrease in the intensity. The emission could be totally extinguished by addition of sufficient SDS. The decrease in light emission is not due to photophysical quenching of the excited state since thermal decomposition in the same solvent system at elevated temperatures results in readily detectable chemiluminescence. (7.) Sequential injection of ten identical aliquots of the dioxetane stock solution when light emission had stopped resulted in identical chemiluminescence decay curves, both in $I_{MAX}$ and time for complete decay of the signal. This experiment shows that the role of the enzyme in the reaction is catalytic.

Competitive Inhibition. Competitive inhibitors are chemically similar substances which may reversibly or irreversibly impede an enzymatic reaction by competing with the substrate of interest for the enzyme binding site(s). If binding of the inhibitor is reversible (e.g. if its products upon reaction at the enzyme do not bind irreversibly) then the enzymatic reaction of a given substrate may be temporarily slowed or stopped by addition of a competing substrate with a greater affinity (binding constant) for the enzyme. When the competing substrate is consumed reaction of the first substrate may resume. If the enzymatic reaction of interest is a chemiluminescent reaction then competitive inhibitors should cause a decrease in light intensity due to the slower rate. In the limit where reaction of the inhibitor is much faster than reaction of the chemiluminescent precursor, this effect should manifest itself as a temporary drop in light intensity until the competitor is consumed followed by restoration of the previous light intensity.

This type of behavior explains the effect of the addition of the known esterase substrates α-naphthyl acetate and β-naphthyl acetate. These substrates were shown by UV spectroscopy to be hydrolyzed by the enzyme in seconds under the reaction conditions. A solution of 25 μL of the dioxetane stock (0.002M) in 3 mL of pH 7.6 phosphate buffer maintained at 37° C. was treated with 5 μL of the enzyme to initiate the chemiluminescence. At the point of maximum emission 10 μL of 0.011M solution of either α- or β-naphthyl acetate were added. A rapid decrease in light intensity was noted followed by restoration of the original intensity within less than one minute.

Stability of Enzyme and Dioxetane to Reaction Conditions. Many dioxetanes are known to be destroyed via a non-luminescent pathway by acid catalyzed processes in aprotic solvents. Similarly, amines are also known to cause the catalytic destruction of dioxetanes via an electron-transfer process. The stability of the dioxetane to the aqueous buffers used in the enzyme reactions, especially Tris buffer, was a matter of concern. A series of experiments were performed to assess the stability of the dioxetane in these buffers over the expected time course of a typical run. A comparison was made between the maximum light intensity produced for a given buffer and temperature with delays of 0 and 30 minutes before the enzyme was added. If the dioxetane were decomposing in the buffer then $I_{MAX}$ of the run where the dioxetane was exposed to the buffer for 30 minutes would be lower provided the enzyme is not saturated. Since constant light levels were not seen in any runs it can be reasonably assumed that saturation kinetics did not apply here. In 0.05M phosphate buffer, pH 7.6 at 25° C. and 37° C. the percent decrease in $I_{MAX}$ due to the 30 minute delay was, respectively, 0 and 7% while in 0.02M Tris buffer, pH 7.6 at 25° C. a 12% decrease was found and at 37° C. after a delay of one hour a 34% decrease occurred.

Figure 2:
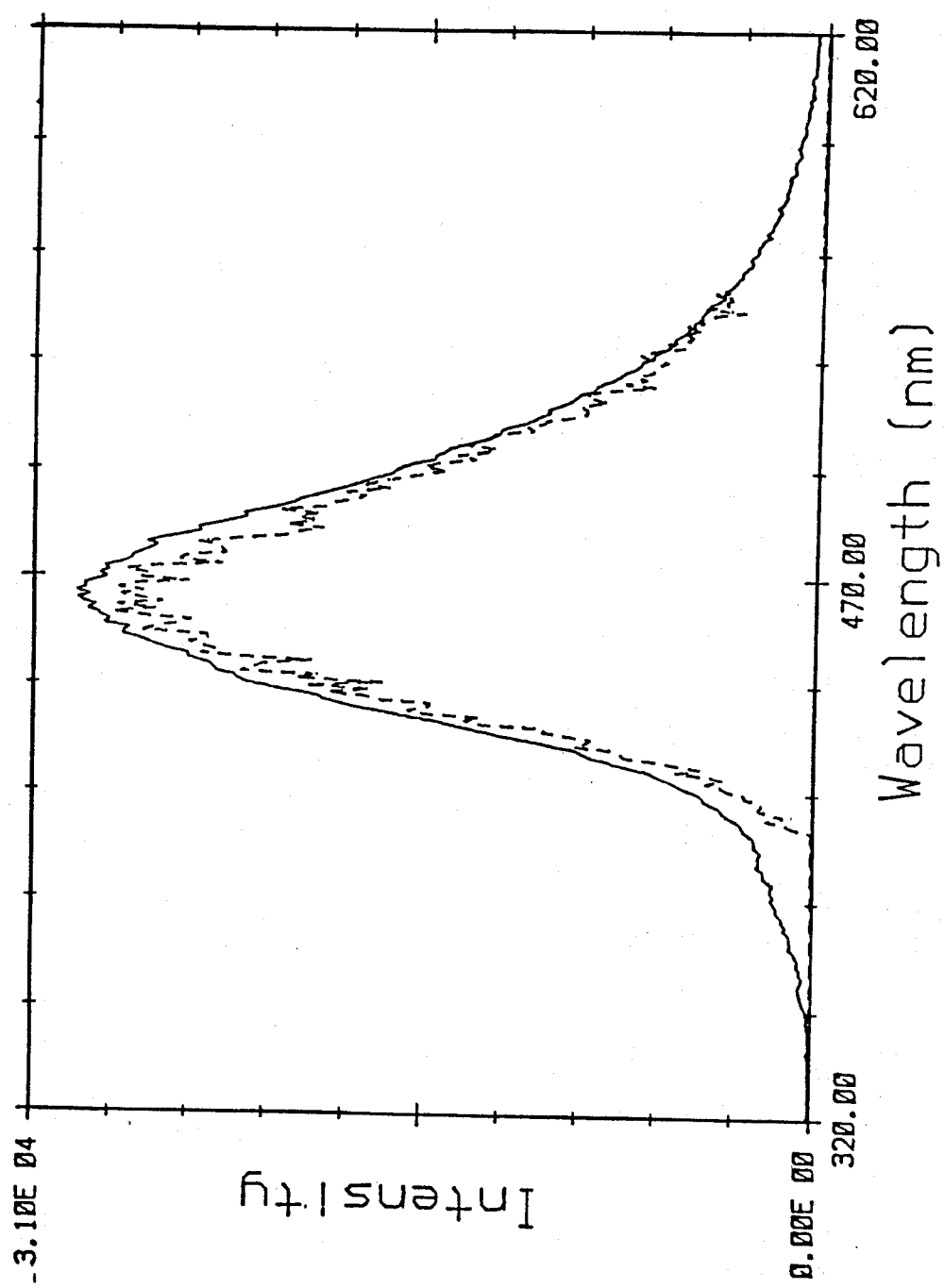
FIG. 2 is a graph showing light intensity as a function of wavelength for compound 2e described hereinafter, and one of its carbonyl containing compound decomposition products, where the activating agent is an enzyme.

Chemiluminescence Spectra. The enzyme-catalyzed decomposition was carried out in Tris buffer, pH 7.6 at room temperature in a standard 1-cm cuvette in the sample compartment of a Spex Fluorolog spectrofluorometer. Scanning the wavelength of the emission revealed that the chemiluminescence spectrum (FIG. 2, dashed line) matched exactly the fluorescence spectrum (solid line) of the expected cleavage product, methyl 6-hydroxy-2-naphthoate, in which the acetate ester protecting group had been removed. The spontaneous chemiluminescence spectrum of the corresponding hydroxy-dioxetane under the same conditions of buffer and pH was also identical. These findings taken together are strong evidence that the chemiluminescence is initiated by rate-limiting hydrolysis of the acetyl group. It proved impossible to excite the fluorescence spectrum of the cleavage product in the spent reaction mixture due to overlapping absorption and very intense fluorescence from the enzyme itself. Interestingly, no emission from the enzyme was detected during the chemiluminescent decomposition even though energy transfer to the enzyme from the excited cleavage product is energetically feasible. This might be explainable if the enzyme binding site is far removed from the fluorophore.

2. Acetylcholinesterase

Acetylcholinesterase, an enzyme of considerable biological significance, hydrolyzes acetylcholine to choline and acetic acid under physiological conditions. It was of interest to determine whether this enzyme would also initiate the chemiluminescent decomposition of the acetyl-protected dioxetane 2e by removal of the acetyl group. Acetylcholinesterase (C-3389) from human erythrocytes was purchased from Sigma Chemical Co. as a lyophilized powder containing phosphate buffer salts. Each mg of protein has an activity of 0.9 Units, 1 Unit being defined as the amount which will hydrolyze 1 micromole of acetylcholine per minute at pH 8.0, 37° C. In a test run in 3 mL of 0.05M phosphate buffer, pH 8.0 at 37.0° C., injection of a 10 μL aliquot of the dioxetane stock solution caused light emission which lasted for 20 seconds. Addition of more dioxetane during this period generated more light. The enzymatic chemiluminescent reaction was reversibly inhibited by the native substrate acetylcholine in the same manner as was described above with esterase and naphthyl acetate.

3. Alkaline Phosphatase

A cuvette containing 3 mL of a buffer solution of 2-amino-2-methyl-1-propanol (Sigma Chemical Co., pH = 10.3, 1.5M) was placed in the black box at 37° C. A portion (200 μL) of the dioxetane stock solution (6d in $CH_2Cl_2$) was added to this buffer solution. Subsequent addition of 10 μL of an alkaline phosphatase suspension [Sigma, Type VII-S from Bovine Intestinal Mucosa, suspension in 3.2M $(NH_4)_2SO_4$] gave rise to chemiluminescence over a period of approximately 2–3 min indicating the enzymatic triggering of the dioxetane. Similar results were obtained with alkaline phosphatase obtained from an alternate biological source (Sigma, Type III from *Escherichia coli*, suspension in 2.5M $(NH_4)_2SO_4$, 100 units/mL).

I claim:

1. In a process for producing a compound of the formula

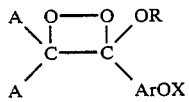

wherein ArOX is an aryl group having an aryl ring substituted with an X-oxy group which forms an unstable oxide intermediate 1,2-dioxetane compound when triggered to remove X by an activating agent so that the unstable 1,2-dioxetane compound decomposes to form light and two carbonyl containing compounds of the formula

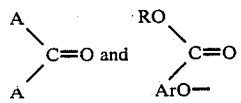

wherein X is a chemically labile group which is removed by the activating agent selected from acid, base, salt, enzyme, inorganic and organic catalysts, and electron donors to form the unstable oxide intermediate 1,2-dioxetane and wherein A and R are passive organic groups which allow the light to be produced wherein the dioxethane is produced by reacting a carbonyl containing compound with an ester compound to form an alkene which forms the dioxetane by reaction with oxygen, the improvement which comprises:

reacting a carbonyl containing compound of the formula:

$$\begin{array}{c} A \\ \phantom{A}\diagdown \\ \phantom{AA}C=O \\ \phantom{A}\diagup \\ A \end{array}$$

with an ester compound of the formula:

$$\begin{array}{c} RO \\ \phantom{RO}\diagdown \\ \phantom{ROO}C=O \\ \phantom{RO}\diagup \\ \text{Ar silyloxy} \end{array}$$

wherein Ar silyloxy in an aryl ring substituted with a silyloxy protecting group in a polar organic solvent in the presence of a metal hydride, a transition metal salt and a tertiary amine base to form an alkene of the formula $$\begin{array}{c} A \phantom{AAAA} OR \\ \phantom{A}\diagdown \phantom{AA} \diagup \\ \phantom{AAA}C=C \\ \phantom{A}\diagup \phantom{AAA}\diagdown \\ A \phantom{AAAA} \text{Ar silyloxy} \end{array}$$

which forms the dioxetane by reaction with oxygen.

2. The process of claim 1 wherein the solvent is tetrahydrofuran and the metal hydride is lithium aluminum hydride.

3. The process of claim 2 wherein the transition metal salt is titanium chloride and the base is triethylamine.

4. The process of claim 1 conducted at the temperature of refluxing tetrahydrofuran.

5. The process of claim 1 wherein in addition the silyl in the silyloxy group in the alkene is replaced with another of X and then reacted with the oxygen to form the dioxetane.

6. The process of claim 5 wherein X with oxy is selected from the group consisting of hydroxyl, inorganic oxy acid salt, phosphate salt, oxygen-pyranoside, aryl and alkyl carboxyl esters.

7. In a process for producing a dioxetane of the formula $$\begin{array}{c} O\phantom{AA}O\phantom{AAA}OR_1 \\ |\phantom{AAAA}|\phantom{A}\diagup \\ R_3C\phantom{A}\text{---}\phantom{A}C \\ \phantom{AAAAAA}\diagdown \\ \phantom{AAAAAAA}R_2OX \end{array} \quad (I)$$

wherein $R_1$ is selected from lower alkyl containing 1 to 8 carbon atoms, $R_2$ is selected from aryl, biaryl and fused ring polycyclic aryl groups which can be substituted or unsubstituted, and $R_3C$— is selected from polycyclic alkyl groups containing 6 to 30 carbon atoms, wherein OX is an X-oxy group substituted on an aryl ring which forms an unstable oxide intermediate 1,2-dioxetane compound when triggered to remove X by an activating agent selected from acid, base salt, enzyme, inorganic and organic catalysts, and electron donor sources and X is a chemically labile group which is removed by the activating agent to form the unstable oxide intermediate and wherein (I) decomposes in the presence of an activating agent to produce light and carbonyl containing compounds of the formula $$R_3C=O \text{ (II) and } \begin{array}{c} R_1O \\ \phantom{R_1O}\diagdown \\ \phantom{R_1OO}C=O \text{ (III)} \\ \phantom{R_1O}\diagup \\ R_2O\text{---} \end{array}$$

wherein the dioxetane is produced by reacting a carbonyl containing compound with an ester compound to form an alkene and which forms the dioxetane by reaction with oxygen, the improvement which comprises:

reacting a carbonyl containing compound of the formula:

$$R_3C=O$$

with an ester compound of the formula:

$$\begin{array}{c} R_1O \\ \phantom{R_1O}\diagdown \\ \phantom{R_1OO}C=O \\ \phantom{R_1O}\diagup \\ R_2 \\ | \\ OA \end{array}$$

wherein OA is a silyloxy protecting group in a polar organic solvent in the presence of a metal hydride, a transition metal salt, and a tertiary amine base to give a vinyl ether of the formula (IV)

$$R_3C=C\begin{array}{c} OR_1 \\ \diagdown \\ R_2OA \end{array} \quad (IV)$$

which forms the dioxetane by reaction with oxygen.

8. The process of claim 7 wherein the solvent is tetrahydrofuran and the metal hydride is lithium aluminum hydride.

9. The process of claim 8 wherein the transition metal salt is titanium chloride and the base is triethylamine.

10. The process of claim 7 conducted at the temperature of refluxing tetetrahydrofuran.

11. The process of claim 7 wherein the silyloxy group in vinyl ether (IV) is converted to a hydroxyl group by reaction of vinyl ether (IV) with tetra-n-butylammonium fluoride trihydrate in tetrahydrofuran to produce a vinyl ether (V) wherein OX is a hydroxyl group.

12. The process of claim 11 wherein the hydroxyl OX group of vinyl ether (V) is converted to an OX group selected from inorganic oxy acid salts, phosphate salt, sulfate salt, oxygen-pyranoside, aryl and alkyl carboxyl esters before oxygenation to yield the corresponding dioxetane (I).

13. The process of claim 7 wherein in addition the group A of the silyloxy protecting group OA in the alkene is replaced with another of X and then reacted with the oxygen to form the dioxetane.

14. The process of claim 13 wherein X with oxy is selected from the gropu consisting of hydroxyl, inorganic oxy acid salt, phosphate salt, oxygen-pyranoside, aryl and alkyl carbonyl esters.

* * * * *

UNITED STATES PATENT AND TRADEMARK OFFICE
CERTIFICATE OF CORRECTION

PATENT NO. : 4,857,652

DATED : August 15, 1989

INVENTOR(S) : Arthur P. Schaap

It is certified that error appears in the above—identified patent and that said Letters Patent is hereby corrected as shown below:

First page under "Other Publications", line 12 "J. Amer. Soc." should be --J. Amer. Chem. Soc.--.

Column 1, line 10, "1,2-dioxanetane" should be --1,2-dioxetane--.

Column 3, line 7, insert a period --.-- after "product".

Column 3, line 8, "dioxetanes" should be --Dioxetanes--.

Column 3, line 47, "New york" should be --New York--.

Column 6, line 12, insert a period --.-- after "product".

Column 6, line 27, "1,2 dioxetane" should be --1,2-dioxetane--.

Column 6, line 47, insert a period --.-- after "intermediate".

Column 7, line 14, "a", second occurrence, should be deleted.

UNITED STATES PATENT AND TRADEMARK OFFICE
CERTIFICATE OF CORRECTION

PATENT NO. : 4,857,652

DATED : August 15, 1989

INVENTOR(S) : Arthur P. Schaap

It is certified that error appears in the above—identified patent and that said Letters Patent is hereby corrected as shown below:

Column 8, line 11, insert a period --.-- after "atoms".

Column 8, line 13, insert a period --.-- after "group" and before "The".

Column 8, line 57, insert a period --.-- after "alkene".

Column 11, line 48, insert a period --.-- after "water" and before "The".

Column 11, line 66, insert a period --.-- after "acid" and before "A".

Column 12, line 2, insert a period --.-- after "mmol)" and before "The".

Column 12, line 8, insert a period --.-- after "color" and before "The".

Column 12, line 44, after "purified" the following should be inserted --further by recrystallization from ether affording a white--.

Column 13, line 14, "114 74, 122 87, 125 38," should be --114.74, 122.87, 125.38,--.

Column 13, line 14, "52,03" should be --52.03--.

Column 13, line 30, "butyldiphenylsilyloxv" should be --butyldiphenylsilyloxy--.

UNITED STATES PATENT AND TRADEMARK OFFICE
CERTIFICATE OF CORRECTION

PATENT NO. : 4,857,652

DATED : August 15, 1989

INVENTOR(S) : Arthur P. Schaap

It is certified that error appears in the above—identified patent and that said Letters Patent is hereby corrected as shown below:

Column 13, lines 63 and 64, "(6-tert-Butyldimethylsilyloxy)-2-naphthyl)methoxymethlene]" should be --[(6-tert-Butyldimethylsilyloxy-2-naphthyl)methoxymethylene]--

Column 14, line 2, insert a period --.-- after "bath" and before "Titanium".

Column 14, line 21, insert a period --.-- after "water" and before "The".

Column 14, line 32, "128,06" should be --128.06--.

Column 14, line 33, "143 73, 153 70;" should be --143.73, 153.70;--.

Column 14, line 58, "ld)" should be --(ld)--.

Column 16, line 18, "6-Acetoxy-2" should be --[(6-Acetoxy-2--.

Column 17, line 29, "33.61" should be --133.61--.

Column 21, line 38, "ammonium}" should be --ammonium)--.

UNITED STATES PATENT AND TRADEMARK OFFICE
CERTIFICATE OF CORRECTION

PATENT NO. : 4,857,652

DATED : August 15, 1989

INVENTOR(S) : Arthur P. Schaap

It is certified that error appears in the above—identified patent and that said Letters Patent is hereby corrected as shown below:

Column 24, line 32, "s, 3H)" should be --(s, 3H)--.

Column 24, line 37, "methoxyspiro]" should be --methoxyspiro [--.

Column 25, line 1, "(CDCl$_{13}$)" should be --CDCl$_3$).

Column 27, line 68, "thylaninomethane" should be --thylaminomethane--.

Column 30, line 68, "dioxethane" should be --dioxetane--.

Column 32, line 64, "gropu" should be --group--.

Column 32, line 68, "carbonyl" should be --carboxyl--.

Signed and Sealed this

Twenty-third Day of October, 1990

Attest:

HARRY F. MANBECK, JR.

*Attesting Officer*      *Commissioner of Patents and Trademarks*